United States Patent
Vivek et al.

(10) Patent No.: US 12,130,910 B2
(45) Date of Patent: Oct. 29, 2024

(54) THRESHOLD SIGNATURE BASED MEDICAL DEVICE MANAGEMENT

(71) Applicant: ICU Medical, Inc., San Clemente, CA (US)

(72) Inventors: S. Sree Vivek, Chennai (IN); Hrishikesh Anil Dandekar, Pune (IN); Chaitanya Mattur Srinivasamurthy, Lake Forest, IL (US)

(73) Assignee: ICU Medical, Inc., San Clemente, CA (US)

( * ) Notice: Subject to any disclaimer, the term of this patent is extended or adjusted under 35 U.S.C. 154(b) by 685 days.

(21) Appl. No.: 16/869,404

(22) Filed: May 7, 2020

(65) Prior Publication Data
US 2020/0353167 A1    Nov. 12, 2020

Related U.S. Application Data

(63) Continuation of application No. PCT/US2020/031664, filed on May 6, 2020.
(Continued)

(51) Int. Cl.
G06F 21/55      (2013.01)
H04L 9/08       (2006.01)
H04L 9/32       (2006.01)

(52) U.S. Cl.
CPC ............ *G06F 21/554* (2013.01); *H04L 9/085* (2013.01); *H04L 9/0894* (2013.01);
(Continued)

(58) Field of Classification Search
CPC .............................. H04L 9/085; H04L 9/3278
See application file for complete search history.

(56) References Cited

U.S. PATENT DOCUMENTS 4,024,864 A     5/1977   Davies et al.
4,055,175 A    10/1977   Clemens et al.
(Continued)

FOREIGN PATENT DOCUMENTS

AU    2004226440    10/2004
AU    2004305087     7/2005
(Continued)

OTHER PUBLICATIONS

M. Nojoumian and D. R. Stinson, "Social secret sharing in cloud computing using a new trust function," 2012 Tenth Annual International Conference on Privacy, Security and Trust, 2012, pp. 161-167, doi: 10.1109/PST.2012.6297936.*
(Continued)

*Primary Examiner* — Jeffrey Nickerson
*Assistant Examiner* — Vadim Savenkov
(74) *Attorney, Agent, or Firm* — Knobbe, Martens, Olson & Bear, LLP

(57) ABSTRACT

The present disclosure is directed to managing device authorization through the use of digital signature thresholds. Individual components of a device, or individual devices in a network environment, are associated with separate secret shares from which a digital signature can be derived. The digital signature may be used to authorize performance of a function. A threshold number of such secret shares are used in order to derive the digital signature. Therefore, an authorization process that relies on digital signature verification to determine that a function is authorized will do so if a threshold number of secret shares are available at authorization time.

18 Claims, 6 Drawing Sheets

Related U.S. Application Data

(60) Provisional application No. 62/845,115, filed on May 8, 2019.

(52) U.S. Cl.
CPC ........ H04L 9/3247 (2013.01); *H04L 2209/16* (2013.01); *H04L 2209/88* (2013.01)

(56) References Cited

U.S. PATENT DOCUMENTS

| | | |
|---|---|---|
| 4,151,845 A | 5/1979 | Clemens |
| 4,213,454 A | 7/1980 | Shim |
| 4,240,438 A | 12/1980 | Updike et al. |
| 4,280,494 A | 7/1981 | Cosgrove et al. |
| 4,308,866 A | 1/1982 | Jeliffe |
| 4,370,983 A | 2/1983 | Lichtenstein et al. |
| 4,373,527 A | 2/1983 | Fischell |
| 4,392,849 A | 7/1983 | Petre et al. |
| 4,395,259 A | 7/1983 | Prestele et al. |
| 4,457,751 A | 7/1984 | Rodler |
| 4,464,170 A | 8/1984 | Clemens |
| 4,469,481 A | 9/1984 | Kobayashi |
| 4,475,901 A | 10/1984 | Kraegen et al. |
| 4,494,950 A | 1/1985 | Fischell |
| 4,498,843 A | 2/1985 | Schneider et al. |
| 4,515,584 A | 5/1985 | Abe et al. |
| 4,526,568 A | 7/1985 | Clemens et al. |
| 4,529,401 A | 7/1985 | Leslie et al. |
| 4,543,955 A | 10/1985 | Schroeppel |
| 4,551,133 A | 11/1985 | Zegers de Beyl et al. |
| 4,553,958 A | 11/1985 | LeCocq |
| 4,559,037 A | 12/1985 | Franetzki et al. |
| 4,613,937 A | 9/1986 | Batty |
| 4,624,661 A | 11/1986 | Arimond |
| 4,633,878 A | 1/1987 | Bombardieri |
| 4,634,426 A | 1/1987 | Kamen |
| 4,634,427 A | 1/1987 | Hannula et al. |
| 4,674,652 A | 6/1987 | Aten et al. |
| 4,676,776 A | 6/1987 | Howson et al. |
| 4,679,562 A | 7/1987 | Luksha |
| 4,685,903 A | 8/1987 | Cable et al. |
| 4,695,954 A | 9/1987 | Rose |
| 4,696,671 A | 9/1987 | Epstein et al. |
| 4,714,462 A | 12/1987 | DiDomenico |
| 4,722,734 A | 2/1988 | Kolin |
| 4,730,849 A | 3/1988 | Siegel |
| 4,731,051 A | 3/1988 | Fischell |
| 4,741,732 A | 5/1988 | Crankshaw et al. |
| 4,756,706 A | 7/1988 | Kerns et al. |
| 4,776,842 A | 10/1988 | Franetzki et al. |
| 4,785,969 A | 11/1988 | Mclaughlin |
| 4,803,625 A | 2/1989 | Fu et al. |
| 4,835,372 A | 5/1989 | Gombrich et al. |
| 4,838,275 A | 6/1989 | Lee |
| 4,838,856 A | 6/1989 | Mulreany et al. |
| 4,838,857 A | 6/1989 | Strowe et al. |
| 4,854,324 A | 8/1989 | Hirschman et al. |
| 4,857,716 A | 8/1989 | Gombrich et al. |
| 4,858,154 A | 8/1989 | Anderson et al. |
| 4,898,578 A | 2/1990 | Rubalcaba, Jr. |
| 4,908,017 A | 3/1990 | Howson et al. |
| 4,933,873 A | 6/1990 | Kaufman et al. |
| 4,943,279 A | 7/1990 | Samiotes et al. |
| 4,946,439 A | 8/1990 | Eggers |
| 4,953,745 A | 9/1990 | Rowlett |
| 4,978,335 A | 12/1990 | Arthur, III |
| 5,000,739 A | 3/1991 | Kulisz et al. |
| 5,010,473 A | 4/1991 | Jacobs |
| 5,014,698 A | 5/1991 | Cohen |
| 5,016,172 A | 5/1991 | Dessertine |
| 5,026,084 A | 6/1991 | Paisfield |
| 5,034,004 A | 7/1991 | Crankshaw |
| 5,041,086 A | 8/1991 | Koenig et al. |
| 5,058,161 A | 10/1991 | Weiss |
| 5,078,683 A | 1/1992 | Sancoff et al. |
| 5,084,828 A | 1/1992 | Kaufman et al. |
| 5,088,981 A | 2/1992 | Howson et al. |
| 5,097,505 A | 3/1992 | Weiss |
| 5,100,380 A | 3/1992 | Epstein et al. |
| 5,102,392 A | 4/1992 | Sakai et al. |
| 5,104,374 A | 4/1992 | Bishko et al. |
| 5,109,850 A | 5/1992 | Blanco et al. |
| 5,131,816 A | 7/1992 | Brown |
| 5,142,484 A | 8/1992 | Kaufman et al. |
| 5,153,827 A | 10/1992 | Coutre et al. |
| 5,157,640 A | 10/1992 | Backner |
| 5,161,222 A | 11/1992 | Montejo et al. |
| 5,177,993 A | 1/1993 | Beckman et al. |
| 5,181,910 A | 1/1993 | Scanlon |
| 5,190,522 A | 3/1993 | Wocicki et al. |
| 5,199,439 A | 4/1993 | Zimmerman et al. |
| 5,200,891 A | 4/1993 | Kehr et al. |
| 5,216,597 A | 6/1993 | Beckers |
| 5,221,268 A | 6/1993 | Barton et al. |
| 5,230,061 A | 7/1993 | Welch |
| 5,243,982 A | 9/1993 | Möstl et al. |
| 5,244,463 A | 9/1993 | Cordner, Jr. et al. |
| 5,249,260 A | 9/1993 | Nigawara et al. |
| 5,254,096 A | 10/1993 | Rondelet et al. |
| 5,256,156 A | 10/1993 | Kern et al. |
| 5,256,157 A | 10/1993 | Samiotes et al. |
| 5,261,702 A | 11/1993 | Mayfield |
| 5,317,506 A | 5/1994 | Coutre et al. |
| 5,319,355 A | 6/1994 | Russek |
| 5,319,363 A | 6/1994 | Welch et al. |
| 5,330,634 A | 7/1994 | Wong et al. |
| 5,338,157 A | 8/1994 | Blomquist |
| 5,341,476 A | 8/1994 | Lowell |
| 5,364,346 A | 11/1994 | Schrezenmeir |
| 5,366,346 A | 11/1994 | Danby |
| 5,368,562 A | 11/1994 | Blomquist et al. |
| 5,373,454 A | 12/1994 | Kanda et al. |
| 5,376,070 A | 12/1994 | Purvis et al. |
| 5,378,231 A | 1/1995 | Johnson et al. |
| 5,389,071 A | 2/1995 | Kawahara et al. |
| 5,389,078 A | 2/1995 | Zalesky et al. |
| 5,417,222 A | 5/1995 | Dempsey et al. |
| 5,423,748 A | 6/1995 | Uhala |
| 5,429,602 A | 7/1995 | Hauser |
| 5,431,627 A | 7/1995 | Pastrone et al. |
| 5,432,777 A | 7/1995 | Le Boudec et al. |
| 5,445,621 A | 8/1995 | Poli et al. |
| 5,447,164 A | 9/1995 | Shaya et al. |
| 5,455,851 A | 10/1995 | Chaco et al. |
| 5,461,365 A | 10/1995 | Schlager et al. |
| 5,464,392 A | 11/1995 | Epstein et al. |
| 5,465,082 A | 11/1995 | Chaco |
| 5,485,408 A | 1/1996 | Blomquist |
| 5,486,286 A | 1/1996 | Peterson et al. |
| 5,493,430 A | 2/1996 | Lu et al. |
| 5,496,273 A | 3/1996 | Pastrone et al. |
| 5,505,828 A | 4/1996 | Wong et al. |
| 5,507,288 A | 4/1996 | Bocker et al. |
| 5,507,786 A | 4/1996 | Morgan et al. |
| 5,508,499 A | 4/1996 | Ferrario |
| 5,515,713 A | 5/1996 | Saugues et al. |
| 5,520,637 A | 5/1996 | Pager et al. |
| 5,522,798 A | 6/1996 | Johnson et al. |
| 5,547,470 A | 8/1996 | Johnson et al. |
| 5,554,013 A | 9/1996 | Owens et al. |
| 5,562,615 A | 10/1996 | Nassif |
| 5,577,169 A | 11/1996 | Prezioso |
| 5,582,323 A | 12/1996 | Kurtenbach |
| 5,582,593 A | 12/1996 | Hultman |
| 5,594,786 A | 1/1997 | Chaco et al. |
| 5,598,519 A | 1/1997 | Narayanan |
| 5,620,608 A | 4/1997 | Rosa et al. |
| 5,630,710 A | 5/1997 | Tune et al. |
| 5,636,044 A | 6/1997 | Yuan et al. |
| 5,643,212 A | 7/1997 | Coutre et al. |
| 5,651,775 A | 7/1997 | Walker et al. |
| 5,658,131 A | 8/1997 | Aoki et al. |
| 5,658,250 A | 8/1997 | Blomquist et al. |
| 5,665,065 A | 9/1997 | Colman et al. |

(56) References Cited

U.S. PATENT DOCUMENTS

| | | |
|---|---|---|
| 5,669,877 A | 9/1997 | Blomquist |
| 5,672,154 A | 9/1997 | Sillén et al. |
| 5,681,285 A | 10/1997 | Ford et al. |
| 5,685,844 A | 11/1997 | Marttila |
| 5,687,717 A | 11/1997 | Halpern et al. |
| 5,689,229 A | 11/1997 | Chaco et al. |
| 5,697,899 A | 12/1997 | Hillman et al. |
| 5,699,509 A | 12/1997 | Gary et al. |
| 5,708,714 A | 1/1998 | Lopez et al. |
| 5,713,350 A | 2/1998 | Yokota et al. |
| 5,713,856 A | 2/1998 | Eggers et al. |
| 5,718,562 A | 2/1998 | Lawless et al. |
| 5,719,761 A | 2/1998 | Gatti et al. |
| 5,733,259 A | 3/1998 | Valcke et al. |
| 5,738,102 A | 4/1998 | Lemelson |
| 5,744,027 A | 4/1998 | Connell et al. |
| 5,752,621 A | 5/1998 | Passamante |
| 5,754,111 A | 5/1998 | Garcia |
| 5,764,034 A | 6/1998 | Bowman et al. |
| 5,764,159 A | 6/1998 | Neftel et al. |
| 5,772,635 A | 6/1998 | Dastur et al. |
| 5,774,865 A | 6/1998 | Glynn |
| 5,778,256 A | 7/1998 | Darbee |
| 5,778,345 A | 7/1998 | McCartney |
| 5,781,442 A | 7/1998 | Engleson et al. |
| 5,782,805 A | 7/1998 | Meinzer et al. |
| 5,788,669 A | 8/1998 | Peterson |
| 5,797,515 A | 8/1998 | Liff et al. |
| 5,800,387 A | 9/1998 | Duffy et al. |
| 5,814,015 A | 9/1998 | Gargano et al. |
| 5,822,544 A | 10/1998 | Chaco et al. |
| 5,822,715 A | 10/1998 | Worthington et al. |
| 5,827,179 A | 10/1998 | Lichter et al. |
| 5,832,448 A | 11/1998 | Brown |
| 5,836,910 A | 11/1998 | Duffy et al. |
| 5,850,344 A | 12/1998 | Conkright |
| 5,867,821 A | 2/1999 | Ballantyne et al. |
| 5,870,733 A | 2/1999 | Bass et al. |
| 5,871,465 A | 2/1999 | Vasko |
| 5,873,731 A | 2/1999 | Predergast |
| 5,885,245 A | 3/1999 | Lynch et al. |
| 5,897,493 A | 4/1999 | Brown |
| 5,897,498 A | 4/1999 | Canfield, II et al. |
| 5,910,252 A | 6/1999 | Truitt et al. |
| 5,912,818 A | 6/1999 | McGrady et al. |
| 5,915,240 A | 6/1999 | Karpf |
| 5,920,054 A | 7/1999 | Uber, III |
| 5,920,263 A | 7/1999 | Huttenhoff et al. |
| 5,924,074 A | 7/1999 | Evans |
| 5,931,764 A | 8/1999 | Freeman et al. |
| 5,935,099 A | 8/1999 | Peterson et al. |
| 5,935,106 A | 8/1999 | Olsen |
| 5,941,846 A | 8/1999 | Duffy et al. |
| 5,956,501 A | 9/1999 | Brown |
| 5,957,885 A | 9/1999 | Bollish et al. |
| 5,960,085 A | 9/1999 | de la Huerga |
| 5,961,448 A | 10/1999 | Swenson et al. |
| 5,967,559 A | 10/1999 | Abramowitz |
| 5,971,594 A | 10/1999 | Sahai et al. |
| 5,975,081 A | 11/1999 | Hood et al. |
| 5,990,838 A | 11/1999 | Burns et al. |
| 5,997,476 A | 12/1999 | Brown |
| 6,000,828 A | 12/1999 | Leet |
| 6,003,006 A | 12/1999 | Colella et al. |
| 6,012,034 A | 1/2000 | Hamparian et al. |
| 6,017,318 A | 1/2000 | Gauthier et al. |
| 6,021,392 A | 2/2000 | Lester et al. |
| 6,024,539 A | 2/2000 | Blomquist |
| 6,024,699 A | 2/2000 | Surwit et al. |
| 6,032,155 A | 2/2000 | de la Huerga |
| 6,032,676 A | 3/2000 | Moore |
| 6,039,251 A | 3/2000 | Holowko et al. |
| 6,070,761 A | 6/2000 | Bloom et al. |
| 6,073,106 A | 6/2000 | Rozen et al. |
| 6,104,295 A | 8/2000 | Gaisser et al. |
| 6,112,182 A | 8/2000 | Akers et al. |
| 6,112,323 A | 8/2000 | Meizlik et al. |
| RE36,871 E | 9/2000 | Epstein et al. |
| 6,115,365 A | 9/2000 | Newberg |
| 6,115,390 A | 9/2000 | Chuah |
| 6,122,536 A | 9/2000 | Sun et al. |
| 6,126,637 A | 10/2000 | Kriesel et al. |
| 6,135,949 A | 10/2000 | Russo et al. |
| 6,150,942 A | 11/2000 | O'Brien |
| 6,151,643 A | 11/2000 | Cheng et al. |
| 6,157,914 A | 12/2000 | Seto et al. |
| 6,159,147 A | 12/2000 | Lichter et al. |
| 6,167,567 A | 12/2000 | Chiles et al. |
| 6,182,667 B1 | 2/2001 | Hanks et al. |
| 6,189,105 B1 | 2/2001 | Lopes |
| 6,195,589 B1 | 2/2001 | Ketcham |
| 6,208,974 B1 | 3/2001 | Campbell et al. |
| 6,222,323 B1 | 4/2001 | Yamashita et al. |
| 6,223,440 B1 | 5/2001 | Rashman |
| 6,226,277 B1 | 5/2001 | Chuah |
| 6,227,371 B1 | 5/2001 | Song |
| 6,234,176 B1 | 5/2001 | Domae et al. |
| 6,241,704 B1 | 6/2001 | Peterson et al. |
| 6,248,067 B1 | 6/2001 | Causey, III et al. |
| 6,249,705 B1 | 6/2001 | Snell |
| 6,257,265 B1 | 7/2001 | Brunner et al. |
| 6,259,355 B1 | 7/2001 | Chaco et al. |
| 6,269,340 B1 | 7/2001 | Ford et al. |
| 6,270,455 B1 | 8/2001 | Brown |
| 6,271,813 B1 | 8/2001 | Palalau |
| 6,277,072 B1 | 8/2001 | Bardy |
| 6,280,380 B1 | 8/2001 | Bardy |
| 6,283,761 B1 | 9/2001 | Joao |
| 6,285,665 B1 | 9/2001 | Chuah |
| 6,292,860 B1 | 9/2001 | Cochcroft, Jr. |
| 6,312,378 B1 | 11/2001 | Bardy |
| 6,327,254 B1 | 12/2001 | Chuah |
| 6,330,008 B1 | 12/2001 | Razdow et al. |
| 6,339,718 B1 | 1/2002 | Zatezalo et al. |
| 6,346,886 B1 | 2/2002 | de la Huerga |
| 6,363,282 B1 | 3/2002 | Nichols et al. |
| 6,371,719 B1 | 4/2002 | Hildebrandt |
| 6,377,548 B1 | 4/2002 | Chuah |
| 6,388,951 B1 | 5/2002 | Matsumoto et al. |
| 6,406,426 B1 | 6/2002 | Reuss et al. |
| 6,408,330 B1 | 6/2002 | de la Huerga |
| 6,418,334 B1 | 7/2002 | Unger et al. |
| 6,427,088 B1 | 7/2002 | Bowman et al. |
| 6,428,483 B1 | 8/2002 | Carlebach |
| 6,442,432 B2 | 8/2002 | Lee |
| 6,469,991 B1 | 10/2002 | Chuah |
| 6,475,180 B2 | 11/2002 | Peterson et al. |
| 6,482,158 B2 | 11/2002 | Mault |
| 6,485,418 B2 | 11/2002 | Yasushi et al. |
| 6,494,694 B2 | 12/2002 | Lawless et al. |
| 6,494,831 B1 | 12/2002 | Koritzinsky |
| 6,497,680 B1 | 12/2002 | Holst et al. |
| 6,514,460 B1 | 2/2003 | Fendrock |
| 6,517,482 B1 | 2/2003 | Eiden et al. |
| 6,519,569 B1 | 2/2003 | White et al. |
| 6,520,930 B2 | 2/2003 | Critchlow et al. |
| 6,540,672 B1 | 4/2003 | Simonsen et al. |
| 6,542,902 B2 | 4/2003 | Dulong et al. |
| 6,544,212 B2 | 4/2003 | Galley et al. |
| 6,544,228 B1 | 4/2003 | Heitmeier |
| 6,546,350 B1 | 4/2003 | Hartmann et al. |
| 6,551,276 B1 | 4/2003 | Mann et al. |
| 6,554,798 B1 | 4/2003 | Mann et al. |
| 6,558,320 B1 | 5/2003 | Causey et al. |
| 6,558,351 B1 | 5/2003 | Steil et al. |
| 6,565,509 B1 | 5/2003 | Say et al. |
| 6,567,416 B1 | 5/2003 | Chuah |
| 6,571,294 B2 | 5/2003 | Simmon et al. |
| 6,572,542 B1 | 6/2003 | Houben et al. |
| 6,572,545 B2 | 6/2003 | Knobbe et al. |
| 6,578,002 B1 | 6/2003 | Derzay et al. |
| 6,581,117 B1 | 6/2003 | Klein et al. |
| 6,587,034 B1 | 7/2003 | Heiman et al. |
| 6,589,229 B1 | 7/2003 | Connelly et al. |

(56) References Cited

U.S. PATENT DOCUMENTS

| | | |
|---|---|---|
| 6,599,281 B1 | 7/2003 | Struys et al. |
| 6,602,191 B2 | 8/2003 | Quy |
| 6,605,072 B2 | 8/2003 | Struys et al. |
| 6,628,809 B1 | 9/2003 | Rowe et al. |
| 6,631,353 B1 | 10/2003 | Davis et al. |
| 6,640,246 B1 | 10/2003 | Gardy, Jr. et al. |
| 6,641,533 B2 | 11/2003 | Causey, III et al. |
| 6,647,299 B2 | 11/2003 | Bourget |
| 6,652,455 B1 | 11/2003 | Kocher |
| 6,653,937 B2 | 11/2003 | Nelson et al. |
| 6,659,947 B1 | 12/2003 | Carter et al. |
| 6,669,630 B1 | 12/2003 | Joliat et al. |
| 6,671,563 B1 | 12/2003 | Engleson et al. |
| 6,673,033 B1 | 1/2004 | Sciulli et al. |
| 6,674,403 B2 | 1/2004 | Gray et al. |
| 6,681,003 B2 | 1/2004 | Linder et al. |
| 6,689,091 B2 | 2/2004 | Bui et al. |
| 6,692,241 B2 | 2/2004 | Watanabe et al. |
| 6,694,191 B2 | 2/2004 | Starkweather et al. |
| 6,694,334 B2 | 2/2004 | DuLong et al. |
| 6,721,286 B1 | 4/2004 | Williams et al. |
| 6,721,582 B2 | 4/2004 | Trepagnier et al. |
| 6,725,200 B1 | 4/2004 | Rost |
| 6,731,989 B2 | 5/2004 | Engleson et al. |
| 6,740,072 B2 | 5/2004 | Starkweather et al. |
| 6,751,651 B2 | 6/2004 | Crockett |
| 6,752,787 B1 | 6/2004 | Causey, III et al. |
| 6,753,830 B2 | 6/2004 | Gelbman |
| 6,758,810 B2 | 7/2004 | Lebel et al. |
| 6,773,396 B2 | 8/2004 | Flach et al. |
| 6,774,786 B1 | 8/2004 | Havekost et al. |
| 6,775,577 B2 | 8/2004 | Crnkovich et al. |
| 6,780,156 B2 | 8/2004 | Haueter et al. |
| 6,790,198 B1 | 9/2004 | White et al. |
| 6,792,470 B2 | 9/2004 | Hakenberg et al. |
| 6,796,956 B2 | 9/2004 | Hartlaub et al. |
| 6,799,149 B2 | 9/2004 | Hartlaub |
| 6,809,653 B1 | 10/2004 | Mann et al. |
| 6,811,534 B2 | 11/2004 | Bowman, IV et al. |
| 6,816,605 B2 | 11/2004 | Rowe et al. |
| 6,839,753 B2 | 1/2005 | Biondi et al. |
| 6,852,104 B2 | 2/2005 | Blomquist |
| 6,859,134 B1 | 2/2005 | Heiman et al. |
| 6,871,211 B2 | 3/2005 | Labounty et al. |
| 6,873,268 B2 | 3/2005 | Lebel et al. |
| 6,876,303 B2 | 4/2005 | Reeder et al. |
| 6,885,881 B2 | 4/2005 | Leonhardt |
| 6,891,525 B2 | 5/2005 | Ogoro |
| 6,892,278 B2 | 5/2005 | Ebergen |
| 6,899,695 B2 | 5/2005 | Herrera |
| 6,915,170 B2 | 7/2005 | Engleson et al. |
| 6,923,763 B1 | 8/2005 | Kovatchev et al. |
| 6,924,781 B1 | 8/2005 | Gelbman |
| 6,928,338 B1 | 8/2005 | Buchser et al. |
| 6,928,490 B1 | 8/2005 | Bucholz et al. |
| 6,936,029 B2 | 8/2005 | Mann et al. |
| 6,945,954 B2 | 9/2005 | Hochman et al. |
| 6,948,492 B2 | 9/2005 | Wemeling et al. |
| 6,958,677 B1 | 10/2005 | Carter |
| 6,958,691 B1 | 10/2005 | Anderson et al. |
| 6,958,705 B2 | 10/2005 | Lebel et al. |
| 6,961,448 B2 | 11/2005 | Nichols et al. |
| 6,969,352 B2 | 11/2005 | Chiang et al. |
| 6,969,865 B2 | 11/2005 | Duchon et al. |
| 6,974,437 B2 | 12/2005 | Lebel et al. |
| 6,979,326 B2 | 12/2005 | Mann et al. |
| 6,980,958 B1 | 12/2005 | Surwit et al. |
| 6,985,870 B2 | 1/2006 | Martucci et al. |
| 6,986,347 B2 | 1/2006 | Hickle |
| 6,997,880 B2 | 2/2006 | Carlebach et al. |
| 6,997,920 B2 | 2/2006 | Mann et al. |
| 6,998,984 B1 | 2/2006 | Zittrain |
| 7,016,752 B1 | 3/2006 | Ruben et al. |
| 7,017,293 B2 | 3/2006 | Riley |
| 7,025,743 B2 | 4/2006 | Mann et al. |
| 7,029,455 B2 | 4/2006 | Flaherty |
| 7,038,584 B2 | 5/2006 | Carter |
| 7,060,031 B2 | 6/2006 | Webb et al. |
| 7,060,059 B2 | 6/2006 | Keith et al. |
| 7,069,552 B2 | 6/2006 | Lindberg et al. |
| 7,072,725 B2 | 7/2006 | Bristol et al. |
| 7,079,035 B2 | 7/2006 | Bock et al. |
| 7,092,943 B2 | 8/2006 | Roese et al. |
| 7,096,072 B2 | 8/2006 | Engleson et al. |
| 7,099,809 B2 | 8/2006 | Dori |
| 7,103,419 B2 | 9/2006 | Engleson et al. |
| 7,103,578 B2 | 9/2006 | Beck et al. |
| 7,107,106 B2 | 9/2006 | Engleson et al. |
| 7,108,680 B2 | 9/2006 | Rohr et al. |
| 7,109,878 B2 | 9/2006 | Mann et al. |
| 7,114,002 B1 | 9/2006 | Okumura et al. |
| 7,117,041 B2 | 10/2006 | Engleson et al. |
| 7,136,645 B2 | 11/2006 | Hanson et al. |
| 7,137,964 B2 | 11/2006 | Flaherty |
| 7,142,190 B2 | 11/2006 | Martinez |
| 7,150,741 B2 | 12/2006 | Erickson et al. |
| 7,153,289 B2 | 12/2006 | Vasko |
| 7,154,397 B2 | 12/2006 | Zerhusen et al. |
| 7,156,807 B2 | 1/2007 | Carter et al. |
| 7,158,030 B2 | 1/2007 | Chung |
| 7,161,484 B2 | 1/2007 | Tsoukalis et al. |
| 7,167,755 B2 | 1/2007 | Seeberger et al. |
| 7,167,920 B2 | 1/2007 | Traversat |
| 7,171,277 B2 | 1/2007 | Engleson et al. |
| 7,171,492 B1 | 1/2007 | Borella et al. |
| 7,181,493 B2 | 2/2007 | English et al. |
| 7,185,288 B2 | 2/2007 | McKeever |
| 7,193,514 B2 | 3/2007 | Ritson |
| 7,197,025 B2 | 3/2007 | Chuah |
| 7,201,734 B2 | 4/2007 | Hickle |
| 7,204,823 B2 | 4/2007 | Estes et al. |
| 7,213,009 B2 | 5/2007 | Pestotnik |
| 7,216,802 B1 | 5/2007 | de la Huerga |
| 7,220,240 B2 | 5/2007 | Struys et al. |
| 7,224,979 B2 | 5/2007 | Singhal et al. |
| 7,229,430 B2 | 6/2007 | Hickle et al. |
| 7,230,529 B2 | 6/2007 | Ketcherside |
| 7,236,936 B2 | 6/2007 | White et al. |
| 7,238,164 B2 | 7/2007 | Childers et al. |
| 7,247,154 B2 | 7/2007 | Hickle |
| 7,248,239 B2 | 7/2007 | Dowling |
| 7,250,856 B2 | 7/2007 | Havekost et al. |
| 7,255,683 B2 | 8/2007 | Vanderveen et al. |
| 7,256,888 B2 | 8/2007 | Staehr et al. |
| 7,258,534 B2 | 8/2007 | Fathallah et al. |
| 7,263,213 B2 | 8/2007 | Rowe |
| 7,267,664 B2 | 9/2007 | Rizzo |
| 7,267,665 B2 | 9/2007 | Steil et al. |
| 7,275,156 B2 | 9/2007 | Balfanz et al. |
| 7,278,983 B2 | 10/2007 | Ireland et al. |
| 7,289,815 B2 | 10/2007 | Gfeller et al. |
| 7,289,948 B1 | 10/2007 | Mohri |
| 7,293,107 B1 | 11/2007 | Hanson et al. |
| 7,295,119 B2 | 11/2007 | Rappaport et al. |
| 7,295,556 B2 | 11/2007 | Roese et al. |
| 7,301,451 B2 | 11/2007 | Hastings |
| 7,308,300 B2 | 12/2007 | Toews et al. |
| 7,315,825 B2 | 1/2008 | Rosenfeld et al. |
| 7,319,386 B2 | 1/2008 | Collins, Jr. et al. |
| 7,324,000 B2 | 1/2008 | Zittrain et al. |
| 7,327,705 B2 | 2/2008 | Fletcher et al. |
| 7,343,224 B2 | 3/2008 | DiGianfilippo et al. |
| 7,346,025 B2 | 3/2008 | Bryson |
| 7,347,836 B2 | 3/2008 | Peterson et al. |
| 7,354,420 B2 | 4/2008 | Steil et al. |
| 7,369,897 B2 | 5/2008 | Boveja et al. |
| 7,369,948 B1 | 5/2008 | Ferenczi et al. |
| 7,383,088 B2 | 6/2008 | Spinelli et al. |
| 7,384,410 B2 | 6/2008 | Eggers et al. |
| 7,398,183 B2 | 7/2008 | Holland et al. |
| 7,398,279 B2 | 7/2008 | Muno, Jr. et al. |
| 7,399,277 B2 | 7/2008 | Saidara et al. |
| 7,402,153 B2 | 7/2008 | Steil et al. |
| 7,420,472 B2 | 9/2008 | Tran |

(56) References Cited

U.S. PATENT DOCUMENTS

| | | |
|---|---|---|
| 7,432,807 B2 | 10/2008 | Schmitt |
| 7,436,454 B2 | 10/2008 | Yamaguchi et al. |
| 7,447,643 B1 | 11/2008 | Olson |
| 7,454,314 B2 | 11/2008 | Holland et al. |
| 7,457,804 B2 | 11/2008 | Uber, III et al. |
| 7,464,040 B2 | 12/2008 | Joao |
| 7,469,213 B1 | 12/2008 | Rao |
| 7,471,994 B2 | 12/2008 | Ford et al. |
| 7,483,756 B2 | 1/2009 | Engleson et al. |
| 7,489,808 B2 | 2/2009 | Gerder |
| 7,490,021 B2 | 2/2009 | Holland et al. |
| 7,490,048 B2 | 2/2009 | Joao |
| 7,491,187 B2 | 2/2009 | Van Den Berghe et al. |
| 7,519,905 B2 | 4/2009 | Kougiouris et al. |
| 7,523,401 B1 | 4/2009 | Aldridge |
| 7,524,304 B2 | 4/2009 | Genosar |
| 7,551,078 B2 | 6/2009 | Carlson |
| 7,559,321 B2 | 7/2009 | Wermeling et al. |
| 7,565,197 B2 | 7/2009 | Haulbrich et al. |
| 7,572,230 B2 | 8/2009 | Neumann et al. |
| 7,578,802 B2 | 8/2009 | Hickle |
| 7,621,009 B2 | 11/2009 | Elhabashy |
| D606,533 S | 12/2009 | De Jong et al. |
| 7,636,718 B1 | 12/2009 | Steen et al. |
| 7,640,172 B2 | 12/2009 | Kuth |
| 7,645,258 B2 | 1/2010 | White et al. |
| 7,647,237 B2 | 1/2010 | Malave et al. |
| 7,662,124 B2 | 2/2010 | Duchon et al. |
| 7,668,731 B2 | 2/2010 | Martucci et al. |
| 7,671,733 B2 | 3/2010 | McNeal et al. |
| 7,678,071 B2 | 3/2010 | Lebel et al. |
| 7,687,678 B2 | 3/2010 | Jacobs |
| 7,697,994 B2 | 4/2010 | VanDanacker et al. |
| 7,698,239 B2 | 4/2010 | Lieuallen |
| 7,705,727 B2 | 4/2010 | Pestotnik |
| 7,724,147 B2 | 5/2010 | Brown et al. |
| 7,739,126 B1 | 6/2010 | Cave |
| 7,746,218 B2 | 6/2010 | Collins, Jr. |
| 7,766,873 B2 | 8/2010 | Moberg et al. |
| 7,776,029 B2 | 8/2010 | Whitehurst et al. |
| 7,776,031 B2 | 8/2010 | Hartlaub et al. |
| 7,785,313 B2 | 8/2010 | Mastrototaro |
| 7,788,369 B2 | 8/2010 | McAllen et al. |
| 7,806,852 B1 | 10/2010 | Jurson |
| 7,806,886 B2 | 10/2010 | Kanderian, Jr. et al. |
| 7,826,981 B2 | 11/2010 | Goode, Jr. et al. |
| 7,835,927 B2 | 11/2010 | Schlotterbeck et al. |
| 7,836,314 B2 | 11/2010 | Chieu |
| 7,856,276 B2 | 12/2010 | Ripart et al. |
| 7,860,583 B2 | 12/2010 | Condurso et al. |
| 7,864,771 B2 | 1/2011 | Tavares et al. |
| 7,868,754 B2 | 1/2011 | Salvat, Jr. |
| 7,871,394 B2 | 1/2011 | Halbert et al. |
| 7,886,231 B2 | 2/2011 | Hopermann et al. |
| 7,895,053 B2 | 2/2011 | Holland et al. |
| 7,896,842 B2 | 3/2011 | Palmroos et al. |
| 7,899,546 B2 | 3/2011 | Sieracki et al. |
| 7,905,710 B2 | 3/2011 | Wang et al. |
| 7,920,061 B2 | 4/2011 | Klein et al. |
| 7,933,780 B2 | 4/2011 | de la Huerga |
| 7,938,796 B2 | 5/2011 | Moubayed |
| 7,945,452 B2 | 5/2011 | Fathallah et al. |
| 7,974,714 B2 | 7/2011 | Hoffberg |
| 7,976,508 B2 | 7/2011 | Hoag |
| 7,996,241 B2 | 8/2011 | Zak |
| 8,034,026 B2 | 10/2011 | Grant |
| 8,038,593 B2 | 10/2011 | Friedman et al. |
| 8,048,040 B2 | 11/2011 | Kiani |
| 8,060,576 B2 | 11/2011 | Chan et al. |
| 8,065,161 B2 | 11/2011 | Howard et al. |
| 8,066,672 B2 | 11/2011 | Mandro |
| 8,075,514 B2 | 12/2011 | Butterfield et al. |
| 8,078,983 B2 | 12/2011 | Davis et al. |
| 8,082,018 B2 | 12/2011 | Duchon et al. |
| 8,082,312 B2 | 12/2011 | Chan et al. |
| 8,095,692 B2 | 1/2012 | Mehta et al. |
| 8,126,730 B2 | 2/2012 | Dicks et al. |
| 8,147,448 B2 | 4/2012 | Sundar et al. |
| 8,149,131 B2 | 4/2012 | Blornquist |
| 8,169,914 B2 | 5/2012 | Bajpai |
| 8,171,094 B2 | 5/2012 | Chan et al. |
| 8,172,798 B2 | 5/2012 | Hungerford et al. |
| 8,185,322 B2 | 5/2012 | Schroeder et al. |
| 8,195,478 B2 | 6/2012 | Petersen et al. |
| 8,206,350 B2 | 6/2012 | Mann et al. |
| 8,219,413 B2 | 7/2012 | Martinez et al. |
| 8,231,578 B2 | 7/2012 | Fathallah et al. |
| 8,234,128 B2 | 7/2012 | Martucci et al. |
| 8,267,892 B2 | 9/2012 | Spencer et al. |
| 8,271,106 B2 | 9/2012 | Wehba et al. |
| 8,287,495 B2 | 10/2012 | Michaud et al. |
| 8,291,337 B2 | 10/2012 | Gannin et al. |
| 8,298,184 B2 | 10/2012 | DiPerna et al. |
| 8,312,272 B1 | 11/2012 | Serenyl et al. |
| 8,352,290 B2 | 1/2013 | Bartz et al. |
| 8,359,338 B2 | 1/2013 | Butterfield et al. |
| 8,380,536 B2 | 2/2013 | Howard et al. |
| 8,387,112 B1 | 2/2013 | Ranjan et al. |
| 8,394,077 B2 | 3/2013 | Jacobson et al. |
| 8,398,592 B2 | 3/2013 | Leibner-Druska |
| 8,403,908 B2 | 3/2013 | Jacobson et al. |
| 8,435,206 B2 | 5/2013 | Evans et al. |
| 8,449,523 B2 | 5/2013 | Brukalo et al. |
| 8,452,953 B2 | 5/2013 | Buck et al. |
| 8,453,645 B2 | 6/2013 | Figueiredo et al. |
| 8,472,630 B2 | 6/2013 | Konrad et al. |
| 8,480,648 B2 | 7/2013 | Burnett et al. |
| 8,486,019 B2 | 7/2013 | White et al. |
| 8,489,427 B2 | 7/2013 | Simpson et al. |
| 8,494,879 B2 | 7/2013 | Davis et al. |
| 8,504,179 B2 | 8/2013 | Blomquist |
| 8,517,990 B2 | 8/2013 | Teel et al. |
| 8,518,021 B2 | 8/2013 | Stewart et al. |
| 8,543,416 B2 | 9/2013 | Palmroos et al. |
| 8,551,038 B2 | 10/2013 | Tsoukalis et al. |
| 8,560,345 B2 | 10/2013 | Wehba et al. |
| 8,567,681 B2 | 10/2013 | Borges et al. |
| 8,577,692 B2 | 11/2013 | Silkaitis et al. |
| 8,579,884 B2 | 11/2013 | Lanier et al. |
| 8,626,530 B1 | 1/2014 | Tran et al. |
| 8,655,676 B2 | 2/2014 | Wehba et al. |
| 8,660,860 B2 | 2/2014 | Wehba et al. |
| 8,662,388 B2 | 3/2014 | Belkin |
| 8,666,769 B2 | 3/2014 | Butler et al. |
| 8,667,293 B2 | 3/2014 | Birtwhistle et al. |
| 8,687,811 B2 | 4/2014 | Nierzwick et al. |
| 8,700,421 B2 | 4/2014 | Feng et al. |
| 8,731,960 B2 | 5/2014 | Butler et al. |
| 8,768,719 B2 | 7/2014 | Wehba et al. |
| 8,771,251 B2 | 7/2014 | Ruchti et al. |
| 8,777,894 B2 | 7/2014 | Butterfield et al. |
| 8,777,895 B2 | 7/2014 | Hsu et al. |
| 8,799,012 B2 | 8/2014 | Butler et al. |
| 8,876,793 B2 | 11/2014 | Ledford et al. |
| 8,886,316 B1 | 11/2014 | Juels |
| 8,922,330 B2 | 12/2014 | Moberg et al. |
| 8,936,565 B2 | 1/2015 | Chawla |
| 8,945,043 B2 | 2/2015 | Lee et al. |
| 8,952,794 B2 | 2/2015 | Bloomquist et al. |
| 8,959,617 B2 | 2/2015 | Newlin et al. |
| 8,998,100 B2 | 4/2015 | Halbert et al. |
| 9,026,370 B2 | 5/2015 | Rubalcaba et al. |
| 9,069,887 B2 | 6/2015 | Gupta et al. |
| 9,077,544 B2 | 7/2015 | Baker et al. |
| 9,089,642 B2 | 7/2015 | Murphy et al. |
| 9,114,217 B2 | 8/2015 | Sur et al. |
| 9,123,077 B2 | 9/2015 | Silkaitis et al. |
| 9,192,712 B2 | 11/2015 | DeBelser et al. |
| 9,240,002 B2 | 1/2016 | Hume et al. |
| 9,292,692 B2 * | 3/2016 | Wallrabenstein ....... G06F 21/57 |
| 9,302,035 B2 | 4/2016 | Marseille et al. |
| 9,313,154 B1 | 4/2016 | Son |
| 9,381,296 B2 | 7/2016 | Arrizza et al. |
| 9,393,362 B2 | 7/2016 | Cozmi et al. |

(56) References Cited

U.S. PATENT DOCUMENTS

| | | | |
|---|---|---|---|
| 9,430,655 B1 * | 8/2016 | Stockton | H04L 9/3236 |
| 9,438,580 B2 * | 9/2016 | Kupper | H04L 9/3271 |
| 9,483,615 B2 | 11/2016 | Roberts | |
| 9,498,583 B2 | 11/2016 | Sur et al. | |
| 9,539,383 B2 | 1/2017 | Kohlbrecher | |
| 9,572,923 B2 | 2/2017 | Howard et al. | |
| 9,594,875 B2 | 3/2017 | Arrizza et al. | |
| 9,604,000 B2 | 3/2017 | Wehba et al. | |
| 9,641,432 B2 | 5/2017 | Jha et al. | |
| 9,649,431 B2 | 5/2017 | Gray et al. | |
| 9,662,436 B2 | 5/2017 | Belkin et al. | |
| 9,690,909 B2 | 6/2017 | Stewart et al. | |
| 9,707,341 B2 | 7/2017 | Dumas, III et al. | |
| 9,717,845 B2 | 8/2017 | Istoc | |
| 9,724,470 B2 | 8/2017 | Day et al. | |
| 9,764,082 B2 | 9/2017 | Day et al. | |
| 9,886,550 B2 | 2/2018 | Lee et al. | |
| 9,943,269 B2 | 4/2018 | Muhsin et al. | |
| 9,967,739 B2 | 5/2018 | Proennecke et al. | |
| 9,971,871 B2 | 5/2018 | Arrizza et al. | |
| 9,995,611 B2 | 6/2018 | Ruchti et al. | |
| 10,022,498 B2 | 7/2018 | Ruchti et al. | |
| 10,042,986 B2 | 8/2018 | Ruchti et al. | |
| 10,046,112 B2 | 8/2018 | Oruklu et al. | |
| 10,166,328 B2 | 1/2019 | Oruklu et al. | |
| 10,173,008 B2 | 1/2019 | Simpson et al. | |
| 10,188,849 B2 | 1/2019 | Fangrow | |
| 10,233,179 B2 | 3/2019 | Ng et al. | |
| 10,238,799 B2 | 3/2019 | Kohlbrecher | |
| 10,238,801 B2 | 3/2019 | Wehba et al. | |
| 10,242,060 B2 | 3/2019 | Butler et al. | |
| 10,300,194 B2 | 5/2019 | Day et al. | |
| 10,311,972 B2 | 6/2019 | Kohlbrecher et al. | |
| 10,314,974 B2 | 6/2019 | Day et al. | |
| 10,333,843 B2 | 6/2019 | Jha et al. | |
| 10,341,866 B1 | 7/2019 | Spencer et al. | |
| 10,409,995 B1 * | 9/2019 | Wasiq | H04L 9/08 |
| 10,430,761 B2 | 10/2019 | Hume et al. | |
| 10,434,246 B2 | 10/2019 | Silkaitis et al. | |
| 10,438,001 B1 * | 10/2019 | Hariprasad | G06F 21/577 |
| 10,452,842 B2 * | 10/2019 | Dhondse | G06N 3/008 |
| 10,453,157 B2 | 10/2019 | Kamen et al. | |
| 10,463,788 B2 | 11/2019 | Day | |
| 10,516,536 B2 | 12/2019 | Rommel | |
| 10,617,815 B2 | 4/2020 | Day et al. | |
| 10,646,651 B2 | 5/2020 | Day et al. | |
| 10,681,207 B1 * | 6/2020 | Johnson | H04M 3/42059 |
| 10,692,595 B2 | 6/2020 | Xavier et al. | |
| 10,728,262 B1 * | 7/2020 | Vaswani | G06F 21/62 |
| 10,740,436 B2 | 8/2020 | Moskal et al. | |
| 10,741,280 B2 | 8/2020 | Xavier et al. | |
| 10,757,219 B2 | 8/2020 | Moskal | |
| 10,765,799 B2 | 9/2020 | Belkin et al. | |
| 10,799,632 B2 | 10/2020 | Kohlbrecher | |
| 10,812,380 B2 | 10/2020 | Jha et al. | |
| 10,861,592 B2 | 12/2020 | Xavier et al. | |
| 10,898,641 B2 | 1/2021 | Day et al. | |
| 10,950,339 B2 | 3/2021 | Xavier et al. | |
| 10,964,428 B2 | 3/2021 | Xavier et al. | |
| 11,013,861 B2 | 5/2021 | Wehba et al. | |
| 11,037,668 B2 | 6/2021 | Ruchti et al. | |
| 11,052,193 B2 | 7/2021 | Day et al. | |
| 11,139,058 B2 | 10/2021 | Xavier et al. | |
| 11,151,290 B2 * | 10/2021 | Karakoyunlu | G06F 21/88 |
| 11,152,108 B2 | 10/2021 | Xavier et al. | |
| 11,152,109 B2 | 10/2021 | Xavier et al. | |
| 11,152,110 B2 | 10/2021 | Xavier et al. | |
| 11,194,810 B2 | 12/2021 | Butler et al. | |
| 11,235,100 B2 | 2/2022 | Howard et al. | |
| 11,289,183 B2 | 3/2022 | Kohlbrecher | |
| 11,309,070 B2 | 4/2022 | Xavier et al. | |
| 11,328,804 B2 | 5/2022 | Xavier et al. | |
| 11,328,805 B2 | 5/2022 | Xavier et al. | |
| 11,373,753 B2 | 6/2022 | Xavier et al. | |
| 11,437,132 B2 | 9/2022 | Xavier et al. | |
| 11,470,000 B2 | 10/2022 | Jha et al. | |
| 11,483,402 B2 | 10/2022 | Xavier et al. | |
| 11,483,403 B2 | 10/2022 | Xavier et al. | |
| 11,501,877 B2 | 11/2022 | Kohlbrecher et al. | |
| 11,571,508 B2 | 2/2023 | Jacobson et al. | |
| 11,574,721 B2 | 2/2023 | Kohlbrecher | |
| 11,574,737 B2 | 2/2023 | Dharwad et al. | |
| 11,587,669 B2 | 2/2023 | Xavier et al. | |
| 11,590,057 B2 | 2/2023 | Tagliamento et al. | |
| 11,594,326 B2 | 2/2023 | Xavier et al. | |
| 11,605,468 B2 | 3/2023 | Jacobson et al. | |
| 11,626,205 B2 | 4/2023 | Arrizza et al. | |
| 11,628,246 B2 | 4/2023 | Day et al. | |
| 11,628,254 B2 | 4/2023 | Day et al. | |
| 11,654,237 B2 | 5/2023 | Wehba et al. | |
| 11,670,416 B2 | 6/2023 | Xavier et al. | |
| 11,763,927 B2 | 9/2023 | Ruchti et al. | |
| 11,783,935 B2 | 10/2023 | Xavier et al. | |
| 11,881,297 B2 | 1/2024 | Xavier et al. | |
| 11,923,076 B2 | 3/2024 | Xavier et al. | |
| 2001/0016056 A1 | 8/2001 | Westphal et al. | |
| 2001/0029178 A1 | 10/2001 | Criss et al. | |
| 2001/0031944 A1 | 10/2001 | Peterson et al. | |
| 2001/0032099 A1 | 10/2001 | Joao | |
| 2001/0037060 A1 | 11/2001 | Thompson et al. | |
| 2001/0044731 A1 | 11/2001 | Coffman et al. | |
| 2001/0048027 A1 | 12/2001 | Walsh | |
| 2001/0051787 A1 | 12/2001 | Haller et al. | |
| 2001/0056358 A1 | 12/2001 | Dulong et al. | |
| 2002/0010595 A1 | 1/2002 | Kapp | |
| 2002/0013551 A1 | 1/2002 | Zaitsu et al. | |
| 2002/0013723 A1 | 1/2002 | Mise | |
| 2002/0015018 A1 | 2/2002 | Shimazu et al. | |
| 2002/0019584 A1 | 2/2002 | Schulze et al. | |
| 2002/0021700 A1 | 2/2002 | Hata et al. | |
| 2002/0026103 A1 | 2/2002 | Norris et al. | |
| 2002/0029776 A1 | 3/2002 | Blomquist | |
| 2002/0032583 A1 | 3/2002 | Joao | |
| 2002/0040208 A1 | 4/2002 | Flaherty et al. | |
| 2002/0040282 A1 | 4/2002 | Bailey et al. | |
| 2002/0044043 A1 | 4/2002 | Chaco et al. | |
| 2002/0044059 A1 | 4/2002 | Reeder et al. | |
| 2002/0082728 A1 | 6/2002 | Mueller et al. | |
| 2002/0087115 A1 | 7/2002 | Hartlaub | |
| 2002/0087116 A1 | 7/2002 | Hartlaub | |
| 2002/0095486 A1 | 7/2002 | Bahl | |
| 2002/0103675 A1 | 8/2002 | Vanelli | |
| 2002/0123905 A1 | 9/2002 | Goodroe et al. | |
| 2002/0143580 A1 | 10/2002 | Bristol et al. | |
| 2002/0152239 A1 | 10/2002 | Bautista-Lloyd et al. | |
| 2002/0154600 A1 | 10/2002 | Ido et al. | |
| 2002/0173702 A1 | 11/2002 | Lebel et al. | |
| 2002/0173875 A1 | 11/2002 | Wallace et al. | |
| 2002/0193679 A1 | 12/2002 | Malave et al. | |
| 2002/0194329 A1 | 12/2002 | Alling | |
| 2003/0009244 A1 | 1/2003 | Engleson | |
| 2003/0013959 A1 | 1/2003 | Grunwald et al. | |
| 2003/0014222 A1 | 1/2003 | Klass et al. | |
| 2003/0014817 A1 | 1/2003 | Gallant et al. | |
| 2003/0025602 A1 | 2/2003 | Medema et al. | |
| 2003/0028082 A1 | 2/2003 | Thompson | |
| 2003/0036683 A1 | 2/2003 | Kehr et al. | |
| 2003/0036744 A1 | 2/2003 | Struys et al. | |
| 2003/0047126 A1 | 3/2003 | Tomaschko | |
| 2003/0047600 A1 | 3/2003 | Nakanishi et al. | |
| 2003/0050621 A1 | 3/2003 | Lebel et al. | |
| 2003/0059750 A1 | 3/2003 | Bindler et al. | |
| 2003/0060688 A1 | 3/2003 | Ciarniello et al. | |
| 2003/0069963 A1 | 4/2003 | Jayant et al. | |
| 2003/0079746 A1 | 5/2003 | Hickle | |
| 2003/0097529 A1 | 5/2003 | Arimilli et al. | |
| 2003/0104982 A1 | 6/2003 | Wittmann et al. | |
| 2003/0105389 A1 | 6/2003 | Noonan et al. | |
| 2003/0106553 A1 | 6/2003 | Vanderveen | |
| 2003/0115358 A1 | 6/2003 | Yun | |
| 2003/0120384 A1 | 6/2003 | Haitin et al. | |
| 2003/0125662 A1 | 7/2003 | Bui | |
| 2003/0130616 A1 | 7/2003 | Steil | |
| 2003/0135087 A1 | 7/2003 | Hickle et al. | |

(56) References Cited

U.S. PATENT DOCUMENTS

| | | |
|---|---|---|
| 2003/0139701 A1 | 7/2003 | White et al. |
| 2003/0140928 A1 | 7/2003 | Bui et al. |
| 2003/0140929 A1 | 7/2003 | Wilkes et al. |
| 2003/0141981 A1 | 7/2003 | Bui et al. |
| 2003/0143746 A1 | 7/2003 | Sage, Jr. |
| 2003/0144878 A1 | 7/2003 | Wilkes et al. |
| 2003/0158749 A1 | 8/2003 | Olchanski et al. |
| 2003/0187338 A1 | 10/2003 | Say et al. |
| 2003/0200116 A1 | 10/2003 | Forrester |
| 2003/0204416 A1 | 10/2003 | Acharya |
| 2003/0204781 A1 | 10/2003 | Peebles et al. |
| 2003/0212364 A1 | 11/2003 | Mann et al. |
| 2003/0212379 A1 | 11/2003 | Bylund et al. |
| 2003/0212821 A1 | 11/2003 | Gillies et al. |
| 2003/0216831 A1 | 11/2003 | Hart et al. |
| 2003/0217962 A1 | 11/2003 | Childers et al. |
| 2004/0008123 A1 | 1/2004 | Carrender et al. |
| 2004/0010786 A1 | 1/2004 | Cool et al. |
| 2004/0015132 A1 | 1/2004 | Brown |
| 2004/0019607 A1 | 1/2004 | Moubayed et al. |
| 2004/0030323 A1 | 2/2004 | Ullestad et al. |
| 2004/0039257 A1 | 2/2004 | Hickle |
| 2004/0057226 A1 | 3/2004 | Berthou et al. |
| 2004/0064341 A1 | 4/2004 | Langan et al. |
| 2004/0064342 A1 | 4/2004 | Browne et al. |
| 2004/0064435 A1 | 4/2004 | Moubayed et al. |
| 2004/0073161 A1 | 4/2004 | Tachibana |
| 2004/0073811 A1 | 4/2004 | Sanin |
| 2004/0077934 A1 | 4/2004 | Massad |
| 2004/0078231 A1 | 4/2004 | Wilkes et al. |
| 2004/0078236 A1 | 4/2004 | Stoodley et al. |
| 2004/0085186 A1 | 5/2004 | Eveland et al. |
| 2004/0104271 A1 | 6/2004 | Martucci et al. |
| 2004/0122530 A1 | 6/2004 | Hansen |
| 2004/0128162 A1 | 7/2004 | Schlotterbeck et al. |
| 2004/0128163 A1 | 7/2004 | Goodman et al. |
| 2004/0133441 A1 | 7/2004 | Brady et al. |
| 2004/0139004 A1 | 7/2004 | Cohen et al. |
| 2004/0145480 A1 | 7/2004 | Despotis |
| 2004/0147034 A1 | 7/2004 | Gore et al. |
| 2004/0167464 A1 | 8/2004 | Ireland et al. |
| 2004/0167465 A1 | 8/2004 | Kohler |
| 2004/0167804 A1 | 8/2004 | Simpson |
| 2004/0172222 A1 | 9/2004 | Simpson et al. |
| 2004/0172283 A1 | 9/2004 | Vanderveen |
| 2004/0172301 A1 | 9/2004 | Mihai et al. |
| 2004/0172302 A1 | 9/2004 | Martucci et al. |
| 2004/0176667 A1 | 9/2004 | Mihai et al. |
| 2004/0176980 A1 | 9/2004 | Bulitta et al. |
| 2004/0176984 A1 | 9/2004 | White et al. |
| 2004/0181314 A1 | 9/2004 | Zaleski |
| 2004/0189708 A1 | 9/2004 | Larcheveque et al. |
| 2004/0193325 A1 | 9/2004 | Bonderud |
| 2004/0193328 A1 | 9/2004 | Butterfield et al. |
| 2004/0204673 A1 | 10/2004 | Flaherty et al. |
| 2004/0215278 A1 | 10/2004 | Stegink et al. |
| 2004/0220517 A1 | 11/2004 | Starkweather et al. |
| 2004/0225252 A1 | 11/2004 | Gillespie et al. |
| 2004/0236240 A1 | 11/2004 | Kraus et al. |
| 2004/0243438 A1 | 12/2004 | Mintz |
| 2004/0254434 A1 | 12/2004 | Goodnow et al. |
| 2005/0010269 A1 | 1/2005 | Lebel et al. |
| 2005/0020886 A1 | 1/2005 | Hutchinson et al. |
| 2005/0021006 A1 | 1/2005 | Tonnies |
| 2005/0027560 A1 | 2/2005 | Cook |
| 2005/0027567 A1 | 2/2005 | Taha |
| 2005/0038311 A1 | 2/2005 | Kuth |
| 2005/0038669 A1 | 2/2005 | Sachdeva et al. |
| 2005/0038680 A1 | 2/2005 | McMahon |
| 2005/0040226 A1 | 2/2005 | Al-Sheikh |
| 2005/0043620 A1 | 2/2005 | Fallows et al. |
| 2005/0049910 A1 | 3/2005 | Lancaster et al. |
| 2005/0055242 A1 | 3/2005 | Bello et al. |
| 2005/0055244 A1 | 3/2005 | Mullan et al. |
| 2005/0065465 A1 | 3/2005 | Lebel et al. |
| 2005/0065817 A1 | 3/2005 | Mihai et al. |
| 2005/0075544 A1 | 4/2005 | Shapiro et al. |
| 2005/0080801 A1 | 4/2005 | Kothandaraman et al. |
| 2005/0086071 A1 | 4/2005 | Fox, Jr. et al. |
| 2005/0086072 A1 | 4/2005 | Fox |
| 2005/0088704 A1 | 4/2005 | Vaschillo et al. |
| 2005/0090808 A1 | 4/2005 | Malave et al. |
| 2005/0099624 A1 | 5/2005 | Staehr |
| 2005/0102162 A1 | 5/2005 | Blumenfeld |
| 2005/0102165 A1 | 5/2005 | Oshita et al. |
| 2005/0102167 A1 | 5/2005 | Kapoor |
| 2005/0102669 A1 | 5/2005 | Marney et al. |
| 2005/0107923 A1 | 5/2005 | Vanderveen |
| 2005/0108057 A1 | 5/2005 | Cohen et al. |
| 2005/0117529 A1 | 6/2005 | Ramos-Escano |
| 2005/0119788 A1 | 6/2005 | Engleson et al. |
| 2005/0119914 A1 | 6/2005 | Batch |
| 2005/0131739 A1 | 6/2005 | Rabinowitz et al. |
| 2005/0135306 A1 | 6/2005 | McAllen et al. |
| 2005/0137522 A1 | 6/2005 | Aoki |
| 2005/0137573 A1 | 6/2005 | McLaughlin |
| 2005/0138428 A1 | 6/2005 | McAllen et al. |
| 2005/0154769 A1 | 7/2005 | Eckart et al. |
| 2005/0160057 A1 | 7/2005 | Wefers et al. |
| 2005/0171503 A1 | 8/2005 | Van Den Berghe et al. |
| 2005/0171815 A1 | 8/2005 | Vanderveen |
| 2005/0177096 A1 | 8/2005 | Bollish et al. |
| 2005/0177395 A1 | 8/2005 | Blomquist |
| 2005/0182306 A1 | 8/2005 | Sloan |
| 2005/0182355 A1 | 8/2005 | Bui |
| 2005/0187950 A1 | 8/2005 | Parker |
| 2005/0192557 A1 | 9/2005 | Brauker et al. |
| 2005/0197554 A1 | 9/2005 | Polcha |
| 2005/0197621 A1 | 9/2005 | Poulsen et al. |
| 2005/0210037 A1 | 9/2005 | Wefers et al. |
| 2005/0216479 A1 | 9/2005 | Wefers et al. |
| 2005/0216480 A1 | 9/2005 | Wefers et al. |
| 2005/0223045 A1 | 10/2005 | Funahashi et al. |
| 2005/0224083 A1 | 10/2005 | Crass |
| 2005/0234746 A1 | 10/2005 | Funahashi |
| 2005/0240305 A1 | 10/2005 | Bogash et al. |
| 2005/0246416 A1 | 11/2005 | Blomquist |
| 2005/0251418 A1 | 11/2005 | Fox, Jr. et al. |
| 2005/0261660 A1 | 11/2005 | Choi |
| 2005/0273059 A1 | 12/2005 | Mernoe et al. |
| 2005/0273367 A1 | 12/2005 | Nourie et al. |
| 2005/0277873 A1 | 12/2005 | Stewart et al. |
| 2005/0277890 A1 | 12/2005 | Stewart et al. |
| 2005/0278194 A1 | 12/2005 | Holland et al. |
| 2006/0004772 A1 | 1/2006 | Hagan et al. |
| 2006/0009727 A1 | 1/2006 | O'Mahony et al. |
| 2006/0009734 A1 | 1/2006 | Martin |
| 2006/0010098 A1 | 1/2006 | Goodnow et al. |
| 2006/0042139 A1 | 3/2006 | Mendes |
| 2006/0047270 A1 | 3/2006 | Shelton |
| 2006/0053036 A1 | 3/2006 | Coffman et al. |
| 2006/0064020 A1 | 3/2006 | Burnes et al. |
| 2006/0074633 A1 | 4/2006 | Mahesh et al. |
| 2006/0074920 A1 | 4/2006 | Wefers et al. |
| 2006/0079831 A1 | 4/2006 | Gilbert |
| 2006/0089539 A1 | 4/2006 | Miodownik et al. |
| 2006/0089854 A1 | 4/2006 | Holland et al. |
| 2006/0089855 A1 | 4/2006 | Holland et al. |
| 2006/0100746 A1 | 5/2006 | Leibner-Druska |
| 2006/0100907 A1 | 5/2006 | Holland et al. |
| 2006/0106649 A1 | 5/2006 | Eggers et al. |
| 2006/0111943 A1 | 5/2006 | Wu |
| 2006/0116904 A1 | 6/2006 | Brem |
| 2006/0116907 A1 | 6/2006 | Rhodes et al. |
| 2006/0122481 A1 | 6/2006 | Sievenpiper et al. |
| 2006/0122867 A1 | 6/2006 | Eggers et al. |
| 2006/0129140 A1 | 6/2006 | Todd et al. |
| 2006/0129429 A1 | 6/2006 | Moubayed et al. |
| 2006/0129434 A1 | 6/2006 | Smitherman et al. |
| 2006/0129435 A1 | 6/2006 | Smitherman et al. |
| 2006/0136266 A1 | 6/2006 | Tarassenko et al. |
| 2006/0136271 A1 | 6/2006 | Eggers et al. |
| 2006/0143051 A1 | 6/2006 | Eggers et al. |
| 2006/0173260 A1 | 8/2006 | Gaoni et al. |

(56) References Cited

U.S. PATENT DOCUMENTS

| | | |
|---|---|---|
| 2006/0173406 A1 | 8/2006 | Hayes et al. |
| 2006/0173715 A1 | 8/2006 | Wang et al. |
| 2006/0173927 A1 | 8/2006 | Beyer et al. |
| 2006/0190302 A1 | 8/2006 | Eggers et al. |
| 2006/0195022 A1 | 8/2006 | Trepagnier et al. |
| 2006/0200007 A1 | 9/2006 | Brockway et al. |
| 2006/0200369 A1 | 9/2006 | Batch et al. |
| 2006/0211404 A1 | 9/2006 | Cromp et al. |
| 2006/0224141 A1 | 10/2006 | Rush et al. |
| 2006/0229918 A1 | 10/2006 | Fotsch et al. |
| 2006/0236373 A1 | 10/2006 | Graves et al. |
| 2006/0247606 A1* | 11/2006 | Batch .............. A61M 5/1413 606/1 |
| 2006/0253554 A1* | 11/2006 | Uwais .............. G06F 21/73 710/36 |
| 2006/0258985 A1 | 11/2006 | Russell |
| 2006/0259327 A1 | 11/2006 | Hoag |
| 2006/0264895 A1 | 11/2006 | Flanders |
| 2006/0267753 A1 | 11/2006 | Hussey et al. |
| 2006/0268710 A1 | 11/2006 | Appanna et al. |
| 2006/0270971 A1 | 11/2006 | Gelfand et al. |
| 2006/0277206 A1 | 12/2006 | Bailey et al. |
| 2006/0287885 A1 | 12/2006 | Frick |
| 2007/0015972 A1 | 1/2007 | Wang et al. |
| 2007/0016443 A1 | 1/2007 | Wachman et al. |
| 2007/0021715 A1 | 1/2007 | Kohlbrenner et al. |
| 2007/0027506 A1 | 2/2007 | Stender et al. |
| 2007/0060796 A1 | 3/2007 | Kim |
| 2007/0060870 A1 | 3/2007 | Tolle et al. |
| 2007/0060871 A1 | 3/2007 | Istoc |
| 2007/0061393 A1 | 3/2007 | Moore |
| 2007/0065363 A1 | 3/2007 | Dalal et al. |
| 2007/0073419 A1 | 3/2007 | Sesay |
| 2007/0078314 A1 | 4/2007 | Grounsell |
| 2007/0083870 A1 | 4/2007 | Kanakogi |
| 2007/0088333 A1 | 4/2007 | Levin et al. |
| 2007/0093786 A1 | 4/2007 | Goldsmith et al. |
| 2007/0100665 A1 | 5/2007 | Brown |
| 2007/0100667 A1 | 5/2007 | Bardy |
| 2007/0106126 A1 | 5/2007 | Mannheimer et al. |
| 2007/0112298 A1 | 5/2007 | Mueller et al. |
| 2007/0116037 A1 | 5/2007 | Moore |
| 2007/0118405 A1 | 5/2007 | Campbell et al. |
| 2007/0135866 A1 | 6/2007 | Baker et al. |
| 2007/0136098 A1 | 6/2007 | Smythe et al. |
| 2007/0142822 A1 | 6/2007 | Remde |
| 2007/0156282 A1 | 7/2007 | Dunn |
| 2007/0156452 A1 | 7/2007 | Batch |
| 2007/0169008 A1 | 7/2007 | Varanasi et al. |
| 2007/0179448 A1 | 8/2007 | Lim et al. |
| 2007/0186923 A1 | 8/2007 | Poutiatine et al. |
| 2007/0191817 A1 | 8/2007 | Martin |
| 2007/0191973 A1 | 8/2007 | Holzbauer et al. |
| 2007/0213657 A1 | 9/2007 | Jennewine et al. |
| 2007/0213684 A1 | 9/2007 | Hickle et al. |
| 2007/0214003 A1 | 9/2007 | Holland et al. |
| 2007/0215545 A1 | 9/2007 | Bissler et al. |
| 2007/0232867 A1 | 10/2007 | Hansmann |
| 2007/0233035 A1 | 10/2007 | Wehba et al. |
| 2007/0233049 A1 | 10/2007 | Wehba et al. |
| 2007/0233206 A1 | 10/2007 | Frikart |
| 2007/0233520 A1 | 10/2007 | Wehba et al. |
| 2007/0240215 A1* | 10/2007 | Flores .............. G06F 21/566 726/24 |
| 2007/0251835 A1 | 11/2007 | Mehta et al. |
| 2007/0253021 A1 | 11/2007 | Mehta et al. |
| 2007/0254593 A1 | 11/2007 | Jollota et al. |
| 2007/0255125 A1 | 11/2007 | Moberg et al. |
| 2007/0257788 A1 | 11/2007 | Carlson |
| 2007/0258395 A1 | 11/2007 | Jollota et al. |
| 2007/0299687 A1 | 12/2007 | Palmer et al. |
| 2007/0299695 A1 | 12/2007 | Jung et al. |
| 2008/0001771 A1 | 1/2008 | Faoro et al. |
| 2008/0004904 A1 | 1/2008 | Tran |
| 2008/0009684 A1 | 1/2008 | Corsetti et al. |
| 2008/0033361 A1 | 2/2008 | Evans et al. |
| 2008/0033966 A1 | 2/2008 | Wahl |
| 2008/0034323 A1 | 2/2008 | Blomquist |
| 2008/0041942 A1 | 2/2008 | Aissa |
| 2008/0052704 A1 | 2/2008 | Wysocki |
| 2008/0065007 A1 | 3/2008 | Peterson et al. |
| 2008/0065417 A1 | 3/2008 | Jung et al. |
| 2008/0071217 A1 | 3/2008 | Moubayed et al. |
| 2008/0071251 A1 | 3/2008 | Moubayed et al. |
| 2008/0086088 A1 | 4/2008 | Malcolm |
| 2008/0091466 A1 | 4/2008 | Butler et al. |
| 2008/0095339 A1 | 4/2008 | Elliott |
| 2008/0097289 A1 | 4/2008 | Steil et al. |
| 2008/0097552 A1 | 4/2008 | Dicks et al. |
| 2008/0126969 A1 | 5/2008 | Blomquist |
| 2008/0139907 A1 | 6/2008 | Rao et al. |
| 2008/0148047 A1 | 6/2008 | Appenzeller et al. |
| 2008/0149117 A1 | 6/2008 | Raghuram |
| 2008/0154177 A1 | 6/2008 | Moubayed et al. |
| 2008/0172337 A1 | 7/2008 | Banfield et al. |
| 2008/0184219 A1 | 7/2008 | Matsumoto |
| 2008/0188796 A1 | 8/2008 | Steil et al. |
| 2008/0214919 A1 | 9/2008 | Harmon et al. |
| 2008/0246748 A1 | 10/2008 | Cassidy et al. |
| 2008/0256305 A1 | 10/2008 | Kwon |
| 2008/0259926 A1 | 10/2008 | Tavares et al. |
| 2008/0262469 A1 | 10/2008 | Bristol et al. |
| 2008/0269714 A1 | 10/2008 | Mastrototaro et al. |
| 2008/0269723 A1 | 10/2008 | Mastrototaro et al. |
| 2008/0275384 A1 | 11/2008 | Mastrototaro et al. |
| 2008/0300572 A1 | 12/2008 | Rankers et al. |
| 2008/0301298 A1 | 12/2008 | Bernardi et al. |
| 2008/0320387 A1 | 12/2008 | Sasaki et al. |
| 2008/0320466 A1 | 12/2008 | Dias |
| 2009/0003554 A1 | 1/2009 | Katis et al. |
| 2009/0005703 A1 | 1/2009 | Fasciano |
| 2009/0005728 A1 | 1/2009 | Weinert et al. |
| 2009/0006061 A1 | 1/2009 | Thukral et al. |
| 2009/0006129 A1 | 1/2009 | Thukral |
| 2009/0006133 A1 | 1/2009 | Weinert |
| 2009/0018495 A1 | 1/2009 | Panduro |
| 2009/0036750 A1 | 2/2009 | Weinstein et al. |
| 2009/0051560 A1 | 2/2009 | Manning et al. |
| 2009/0054743 A1 | 2/2009 | Stewart |
| 2009/0054754 A1 | 2/2009 | McMahon et al. |
| 2009/0057399 A1 | 3/2009 | Sajkowsky |
| 2009/0063187 A1 | 3/2009 | Johnson et al. |
| 2009/0069785 A1 | 3/2009 | Miller et al. |
| 2009/0099867 A1 | 4/2009 | Newman |
| 2009/0135196 A1 | 5/2009 | Holland et al. |
| 2009/0143662 A1 | 6/2009 | Estes et al. |
| 2009/0149743 A1 | 6/2009 | Barron et al. |
| 2009/0150174 A1 | 6/2009 | Buck et al. |
| 2009/0150439 A1 | 6/2009 | Gejdos et al. |
| 2009/0150878 A1 | 6/2009 | Pathak et al. |
| 2009/0156991 A1 | 6/2009 | Roberts |
| 2009/0157695 A1 | 6/2009 | Roberts |
| 2009/0158274 A1 | 6/2009 | Roberts |
| 2009/0177146 A1 | 7/2009 | Nesbitt et al. |
| 2009/0177769 A1 | 7/2009 | Roberts |
| 2009/0177992 A1 | 7/2009 | Rubalcaba et al. |
| 2009/0183147 A1 | 7/2009 | Davis et al. |
| 2009/0209938 A1 | 8/2009 | Aalto-Setala |
| 2009/0210250 A1 | 8/2009 | Prax et al. |
| 2009/0221890 A1 | 9/2009 | Saffer et al. |
| 2009/0231249 A1 | 9/2009 | Wang et al. |
| 2009/0270833 A1 | 10/2009 | DeBelser |
| 2009/0275886 A1 | 11/2009 | Bloomquist et al. |
| 2009/0275896 A1 | 11/2009 | Kamen et al. |
| 2009/0284691 A1 | 11/2009 | Marhefka et al. |
| 2009/0292340 A1 | 11/2009 | Mass et al. |
| 2009/0306573 A1 | 12/2009 | Gagner et al. |
| 2009/0326340 A1 | 12/2009 | Wang |
| 2009/0326516 A1 | 12/2009 | Bangera et al. |
| 2010/0008377 A1 | 1/2010 | Hasti et al. |
| 2010/0022988 A1 | 1/2010 | Wochner |
| 2010/0036310 A1 | 2/2010 | Hillman |
| 2010/0056992 A1 | 3/2010 | Hayter |
| 2010/0083060 A1 | 4/2010 | Rahman |

(56) References Cited

U.S. PATENT DOCUMENTS

| | | |
|---|---|---|
| 2010/0095229 A1 | 4/2010 | Dixon et al. |
| 2010/0121170 A1 | 5/2010 | Rule |
| 2010/0121246 A1 | 5/2010 | Peters et al. |
| 2010/0121415 A1 | 5/2010 | Skelton et al. |
| 2010/0121654 A1 | 5/2010 | Portnoy et al. |
| 2010/0121752 A1 | 5/2010 | Banigan et al. |
| 2010/0130933 A1 | 5/2010 | Holland et al. |
| 2010/0131434 A1 | 5/2010 | Magent et al. |
| 2010/0138523 A1 | 6/2010 | Umess et al. |
| 2010/0146137 A1 | 6/2010 | Wu et al. |
| 2010/0156633 A1 | 6/2010 | Buck et al. |
| 2010/0160854 A1 | 6/2010 | Gauthier |
| 2010/0160860 A1 | 6/2010 | Celentano et al. |
| 2010/0174266 A1 | 7/2010 | Estes |
| 2010/0191525 A1 | 7/2010 | Rabenko et al. |
| 2010/0198034 A1 | 8/2010 | Thomas et al. |
| 2010/0198196 A1 | 8/2010 | Wei |
| 2010/0200506 A1 | 8/2010 | Ware et al. |
| 2010/0209268 A1 | 8/2010 | Davis |
| 2010/0212675 A1 | 8/2010 | Walling et al. |
| 2010/0217621 A1 | 8/2010 | Schoenberg |
| 2010/0234708 A1 | 9/2010 | Buck et al. |
| 2010/0250732 A1 | 9/2010 | Bucknell |
| 2010/0271479 A1 | 10/2010 | Heydlauf |
| 2010/0273738 A1 | 10/2010 | Valcke et al. |
| 2010/0274218 A1 | 10/2010 | Yodfat et al. |
| 2010/0280486 A1 | 11/2010 | Khair et al. |
| 2010/0292634 A1 | 11/2010 | Kircher |
| 2010/0298765 A1 | 11/2010 | Budiman et al. |
| 2010/0318025 A1 | 12/2010 | John |
| 2011/0001605 A1 | 1/2011 | Kiani et al. |
| 2011/0021898 A1 | 1/2011 | Wei et al. |
| 2011/0028885 A1 | 2/2011 | Eggers et al. |
| 2011/0040158 A1 | 2/2011 | Katz et al. |
| 2011/0060758 A1 | 3/2011 | Schlotterbeck et al. |
| 2011/0071844 A1 | 3/2011 | Cannon et al. |
| 2011/0072379 A1 | 3/2011 | Gannon |
| 2011/0078253 A1 | 3/2011 | Chan et al. |
| 2011/0078608 A1 | 3/2011 | Gannon et al. |
| 2011/0093284 A1 | 4/2011 | Dicks et al. |
| 2011/0099313 A1 | 4/2011 | Bolanowski |
| 2011/0125095 A1 | 5/2011 | Lebel et al. |
| 2011/0138185 A1 | 6/2011 | Ju et al. |
| 2011/0166628 A1* | 7/2011 | Jain .................. G16H 40/67 709/217 |
| 2011/0175728 A1 | 7/2011 | Baker, Jr. |
| 2011/0178462 A1 | 7/2011 | Moberg et al. |
| 2011/0185010 A1 | 7/2011 | Shatsky et al. |
| 2011/0196748 A1 | 8/2011 | Caron et al. |
| 2011/0231216 A1 | 9/2011 | Fyke et al. |
| 2011/0252230 A1 | 10/2011 | Segre et al. |
| 2011/0257496 A1 | 10/2011 | Terashima et al. |
| 2011/0257798 A1 | 10/2011 | Ali et al. |
| 2011/0259954 A1 | 10/2011 | Bartz et al. |
| 2011/0264043 A1 | 10/2011 | Kotnick et al. |
| 2011/0264044 A1 | 10/2011 | Bartz et al. |
| 2011/0266221 A1 | 11/2011 | Ware et al. |
| 2011/0270045 A1 | 11/2011 | Lebel et al. |
| 2011/0275904 A1 | 11/2011 | Lebel et al. |
| 2011/0286457 A1 | 11/2011 | Ee |
| 2011/0289314 A1 | 11/2011 | Whitcomb |
| 2011/0289497 A1 | 11/2011 | Kiaie et al. |
| 2011/0295196 A1 | 12/2011 | Chazot et al. |
| 2011/0295341 A1 | 12/2011 | Estes et al. |
| 2011/0296051 A1 | 12/2011 | Vange |
| 2011/0296411 A1 | 12/2011 | Tang et al. |
| 2011/0313789 A1 | 12/2011 | Karmen et al. |
| 2011/0319813 A1 | 12/2011 | Kamen et al. |
| 2011/0320049 A1 | 12/2011 | Chossat et al. |
| 2012/0005680 A1 | 1/2012 | Dolby et al. |
| 2012/0011253 A1 | 1/2012 | Friedman et al. |
| 2012/0016305 A1 | 1/2012 | Jollota |
| 2012/0029941 A1 | 2/2012 | Malave et al. |
| 2012/0036102 A1 | 2/2012 | Fletcher et al. |
| 2012/0036550 A1* | 2/2012 | Rodriguez .............. G06F 21/57 726/1 |
| 2012/0066501 A1 | 3/2012 | Xiong |
| 2012/0070045 A1 | 3/2012 | Vesper et al. |
| 2012/0095437 A1 | 4/2012 | Hemmerling |
| 2012/0112903 A1 | 5/2012 | Kaib et al. |
| 2012/0130198 A1 | 5/2012 | Beaule |
| 2012/0143116 A1 | 6/2012 | Ware et al. |
| 2012/0150556 A1 | 6/2012 | Galasso et al. |
| 2012/0157920 A1 | 6/2012 | Flachbart et al. |
| 2012/0179135 A1 | 7/2012 | Rinehart et al. |
| 2012/0179136 A1 | 7/2012 | Rinehart et al. |
| 2012/0185267 A1 | 7/2012 | Kamen et al. |
| 2012/0203177 A1 | 8/2012 | Lanier |
| 2012/0245554 A1 | 9/2012 | Kawamura |
| 2012/0259978 A1 | 10/2012 | Petersen et al. |
| 2012/0260012 A1 | 10/2012 | Gao-Saari et al. |
| 2012/0277716 A1 | 11/2012 | Ali et al. |
| 2012/0283630 A1 | 11/2012 | Lee et al. |
| 2012/0284734 A1 | 11/2012 | McQuaid et al. |
| 2012/0323212 A1 | 12/2012 | Murphy |
| 2012/0330380 A1 | 12/2012 | Corndorf |
| 2013/0006666 A1 | 1/2013 | Schneider |
| 2013/0006702 A1 | 1/2013 | Wu |
| 2013/0012877 A1 | 1/2013 | Debelser et al. |
| 2013/0012879 A1 | 1/2013 | Debelser et al. |
| 2013/0012880 A1 | 1/2013 | Blomquist |
| 2013/0015980 A1 | 1/2013 | Evans et al. |
| 2013/0036403 A1 | 2/2013 | Geist |
| 2013/0036412 A1 | 2/2013 | Birtwhistle et al. |
| 2013/0066265 A1 | 3/2013 | Grant |
| 2013/0072872 A1 | 3/2013 | Yodfat et al. |
| 2013/0091350 A1 | 4/2013 | Gluck |
| 2013/0096444 A1 | 4/2013 | Condurso et al. |
| 2013/0096648 A1 | 4/2013 | Benson |
| 2013/0102963 A1 | 4/2013 | Marsh et al. |
| 2013/0114594 A1 | 5/2013 | Van Zijst |
| 2013/0116578 A1* | 5/2013 | An .................. A61B 5/7275 600/484 |
| 2013/0138452 A1 | 5/2013 | Cork et al. |
| 2013/0144206 A1 | 6/2013 | Lee et al. |
| 2013/0150824 A1 | 6/2013 | Estes et al. |
| 2013/0167245 A1 | 6/2013 | Birtwhistle et al. |
| 2013/0173473 A1 | 7/2013 | Birtwhistle et al. |
| 2013/0191770 A1 | 7/2013 | Bartz et al. |
| 2013/0204188 A1 | 8/2013 | Kamen et al. |
| 2013/0218080 A1 | 8/2013 | Peterfreund et al. |
| 2013/0274669 A1 | 10/2013 | Stempfle et al. |
| 2013/0275539 A1 | 10/2013 | Gross et al. |
| 2013/0291116 A1 | 10/2013 | Homer |
| 2013/0296823 A1 | 11/2013 | Melker et al. |
| 2013/0296984 A1 | 11/2013 | Burnett et al. |
| 2013/0317753 A1 | 11/2013 | Kamen et al. |
| 2013/0346108 A1 | 12/2013 | Kamen et al. |
| 2014/0025392 A1 | 1/2014 | Chandrasenan |
| 2014/0142540 A1 | 5/2014 | Imhof |
| 2014/0142963 A1 | 5/2014 | Hill et al. |
| 2014/0163517 A1 | 6/2014 | Finan et al. |
| 2014/0172994 A1 | 6/2014 | Raumann et al. |
| 2014/0180711 A1 | 6/2014 | Kamen et al. |
| 2014/0197950 A1 | 7/2014 | Shupp et al. |
| 2014/0215490 A1 | 7/2014 | Mathur et al. |
| 2014/0257251 A1 | 9/2014 | Bush et al. |
| 2014/0266790 A1 | 9/2014 | Al-Ali et al. |
| 2014/0266794 A1 | 9/2014 | Brown et al. |
| 2014/0269643 A1 | 9/2014 | Sun |
| 2014/0276571 A1 | 9/2014 | Ludolph |
| 2014/0280522 A1 | 9/2014 | Watte |
| 2014/0288947 A1 | 9/2014 | Simpson et al. |
| 2014/0294177 A1 | 10/2014 | Shastry et al. |
| 2014/0297329 A1 | 10/2014 | Rock |
| 2014/0316819 A1 | 10/2014 | Dunsirn et al. |
| 2014/0318639 A1 | 10/2014 | Peret et al. |
| 2014/0366878 A1 | 12/2014 | Baron |
| 2014/0371543 A1 | 12/2014 | Steinhauer et al. |
| 2015/0005935 A1 | 1/2015 | Bae et al. |
| 2015/0006907 A1 | 1/2015 | Brouwer et al. |
| 2015/0045729 A1 | 2/2015 | Denzer et al. |
| 2015/0058960 A1 | 2/2015 | Schmoyer et al. |

(56) References Cited

U.S. PATENT DOCUMENTS

| | | |
|---|---|---|
| 2015/0066531 A1 | 3/2015 | Jacobson et al. |
| 2015/0081894 A1 | 3/2015 | Blomquist |
| 2015/0100038 A1 | 4/2015 | McCann et al. |
| 2015/0100787 A1 | 4/2015 | Westin et al. |
| 2015/0117234 A1 | 4/2015 | Raman et al. |
| 2015/0151051 A1 | 6/2015 | Tsoukalis |
| 2015/0161354 A1 | 6/2015 | Blomquist |
| 2015/0199192 A1 | 7/2015 | Borges et al. |
| 2015/0199485 A1 | 7/2015 | Borges et al. |
| 2015/0230760 A1 | 8/2015 | Schneider |
| 2015/0281128 A1 | 10/2015 | Sindhu |
| 2015/0325064 A1* | 11/2015 | Downey ............... G08G 5/0039 701/29.3 |
| 2015/0328396 A1 | 11/2015 | Adams et al. |
| 2015/0352301 A1 | 12/2015 | Stedman et al. |
| 2015/0371004 A1 | 12/2015 | Jones |
| 2015/0379237 A1 | 12/2015 | Mills et al. |
| 2016/0001003 A1 | 1/2016 | Perazzo et al. |
| 2016/0006695 A1 | 1/2016 | Prodoehl et al. |
| 2016/0015885 A1 | 1/2016 | Pananen et al. |
| 2016/0034655 A1 | 2/2016 | Gray et al. |
| 2016/0045661 A1 | 2/2016 | Gray et al. |
| 2016/0051749 A1 | 2/2016 | Istoc |
| 2016/0063471 A1* | 3/2016 | Kobres .................. G06Q 20/40 705/18 |
| 2016/0158437 A1 | 6/2016 | Biasi et al. |
| 2016/0228633 A1 | 8/2016 | Welsch et al. |
| 2016/0241391 A1 | 8/2016 | Fenster |
| 2016/0277152 A1 | 9/2016 | Xiang et al. |
| 2016/0285876 A1 | 9/2016 | Perez et al. |
| 2016/0317742 A1 | 11/2016 | Gannon et al. |
| 2016/0350513 A1 | 12/2016 | Jacobson et al. |
| 2016/0378618 A1* | 12/2016 | Cmielowski ........ G06F 11/3612 714/38.1 |
| 2017/0034277 A1 | 2/2017 | Jackson et al. |
| 2017/0063559 A1* | 3/2017 | Wallrabenstein ....... H04L 9/085 |
| 2017/0099148 A1 | 4/2017 | Ochmanski et al. |
| 2017/0104645 A1 | 4/2017 | Wooton et al. |
| 2017/0111301 A1 | 4/2017 | Robinson |
| 2017/0140134 A1 | 5/2017 | Brough et al. |
| 2017/0146381 A1 | 5/2017 | Eckel et al. |
| 2017/0149567 A1 | 5/2017 | Moskal |
| 2017/0149929 A1 | 5/2017 | Moskal |
| 2017/0214762 A1 | 7/2017 | Swain et al. |
| 2017/0258401 A1 | 9/2017 | Volpe |
| 2017/0258986 A1 | 9/2017 | Tsoiukalis |
| 2017/0262590 A1 | 9/2017 | Karakosta et al. |
| 2017/0274140 A1 | 9/2017 | Howard et al. |
| 2017/0286637 A1 | 10/2017 | Arrizza et al. |
| 2017/0325091 A1 | 11/2017 | Freeman et al. |
| 2017/0351841 A1 | 12/2017 | Moskal |
| 2018/0063724 A1 | 3/2018 | Zhang et al. |
| 2018/0121613 A1 | 5/2018 | Connely, IV et al. |
| 2018/0122502 A1 | 5/2018 | Jones et al. |
| 2018/0126067 A1 | 5/2018 | Ledford et al. |
| 2018/0157821 A1* | 6/2018 | Fan ........................ G06F 21/44 |
| 2018/0181712 A1 | 6/2018 | Ensey et al. |
| 2018/0247712 A1 | 8/2018 | Muhsin et al. |
| 2018/0272117 A1 | 9/2018 | Fangrow |
| 2018/0278594 A1 | 9/2018 | Schiffman et al. |
| 2018/0317826 A1 | 11/2018 | Muhsin et al. |
| 2018/0322948 A1 | 11/2018 | Drost et al. |
| 2018/0359085 A1 | 12/2018 | Dervyn |
| 2019/0006044 A1 | 1/2019 | Brask |
| 2019/0030329 A1 | 1/2019 | Hannaman et al. |
| 2019/0036688 A1 | 1/2019 | Wasily et al. |
| 2019/0096518 A1 | 3/2019 | Pace |
| 2019/0132196 A1 | 5/2019 | Trivedi et al. |
| 2019/0147998 A1 | 5/2019 | Ruchti et al. |
| 2019/0166501 A1* | 5/2019 | Debates ................ H04W 12/12 |
| 2019/0172590 A1 | 6/2019 | Vesto et al. |
| 2019/0207965 A1* | 7/2019 | Espinosa .................. G06F 8/65 |
| 2019/0228863 A1 | 7/2019 | Dharwad et al. |
| 2019/0229982 A1 | 7/2019 | Ikuta et al. |
| 2019/0240405 A1 | 8/2019 | Wehba et al. |
| 2019/0243829 A1 | 8/2019 | Butler et al. |
| 2019/0244689 A1 | 8/2019 | Atkin |
| 2019/0245942 A1 | 8/2019 | Moskal |
| 2019/0269852 A1 | 9/2019 | Kohlbrecher |
| 2019/0311803 A1 | 10/2019 | Kohlbrecher et al. |
| 2019/0348160 A1 | 11/2019 | Heavelyn et al. |
| 2019/0392929 A1 | 12/2019 | Gassman |
| 2020/0023127 A1 | 1/2020 | Simpson et al. |
| 2020/0027541 A1 | 1/2020 | Xavier et al. |
| 2020/0027542 A1 | 1/2020 | Xavier et al. |
| 2020/0027543 A1 | 1/2020 | Xavier et al. |
| 2020/0027548 A1 | 1/2020 | Xavier et al. |
| 2020/0027549 A1 | 1/2020 | Xavier et al. |
| 2020/0027550 A1 | 1/2020 | Xavier et al. |
| 2020/0027551 A1 | 1/2020 | Xavier et al. |
| 2020/0028837 A1 | 1/2020 | Xavier et al. |
| 2020/0028914 A1 | 1/2020 | Xavier et al. |
| 2020/0035355 A1 | 1/2020 | Xavier et al. |
| 2020/0054825 A1 | 2/2020 | Kamen et al. |
| 2020/0061291 A1 | 2/2020 | Day et al. |
| 2020/0145332 A1 | 5/2020 | Jha et al. |
| 2020/0153627 A1* | 5/2020 | Wentz ................... H04L 9/3239 |
| 2020/0206413 A1 | 7/2020 | Silkaitis et al. |
| 2020/0220865 A1* | 7/2020 | Finger .................. H04W 8/265 |
| 2020/0282139 A1 | 9/2020 | Susi |
| 2020/0334497 A1 | 10/2020 | Barrett et al. |
| 2020/0335194 A1 | 10/2020 | Jacobson et al. |
| 2020/0351376 A1 | 11/2020 | Moskal |
| 2020/0353168 A1 | 11/2020 | Keenan et al. |
| 2021/0014259 A1 | 1/2021 | Harris et al. |
| 2021/0045640 A1 | 2/2021 | Poltorak |
| 2021/0085855 A1 | 3/2021 | Belkin et al. |
| 2021/0252210 A1 | 8/2021 | Day et al. |
| 2021/0375421 A1 | 12/2021 | Ruchti et al. |
| 2021/0375438 A1 | 12/2021 | Xavier et al. |
| 2021/0409362 A1 | 12/2021 | Katis et al. |
| 2022/0023535 A1 | 1/2022 | Day |
| 2022/0037011 A1 | 2/2022 | Fryman |
| 2022/0037012 A1 | 2/2022 | Fryman |
| 2022/0051777 A1 | 2/2022 | Xavier et al. |
| 2022/0062541 A1 | 3/2022 | Kamen et al. |
| 2022/0129452 A1 | 4/2022 | Butler et al. |
| 2022/0139536 A1 | 5/2022 | Xavier et al. |
| 2022/0139537 A1 | 5/2022 | Xavier et al. |
| 2022/0139538 A1 | 5/2022 | Xavier et al. |
| 2022/0150307 A1 | 5/2022 | Walsh et al. |
| 2022/0165404 A1 | 5/2022 | Vivek et al. |
| 2022/0189605 A1 | 6/2022 | Kelly et al. |
| 2022/0223283 A1 | 7/2022 | Biasi et al. |
| 2022/0270736 A1 | 8/2022 | Kohlbrecher |
| 2022/0328175 A1 | 10/2022 | Arrizza et al. |
| 2022/0331513 A1 | 10/2022 | Howard et al. |
| 2022/0344023 A1 | 10/2022 | Xavier et al. |
| 2022/0375565 A1 | 11/2022 | Xavier et al. |
| 2022/0384059 A1 | 12/2022 | Xavier et al. |
| 2023/0009405 A1 | 1/2023 | Xavier et al. |
| 2023/0009417 A1 | 1/2023 | Xavier et al. |
| 2023/0139360 A1 | 5/2023 | Kohlbrecher et al. |
| 2023/0145267 A1 | 5/2023 | Xavier et al. |
| 2023/0147762 A1 | 5/2023 | Xavier et al. |
| 2023/0166026 A1 | 6/2023 | Jacobson et al. |
| 2023/0188465 A1 | 6/2023 | Jha et al. |
| 2023/0253108 A1 | 8/2023 | Dharwad et al. |
| 2023/0285660 A1 | 9/2023 | Day et al. |
| 2023/0298768 A1 | 9/2023 | Jacobson et al. |
| 2023/0320935 A1 | 10/2023 | Tagliamento |
| 2023/0321350 A1 | 10/2023 | Day |
| 2023/0321351 A1 | 10/2023 | Wehba et al. |
| 2023/0326570 A1 | 10/2023 | Kohlbrecher |
| 2023/0410989 A1 | 12/2023 | Xavier et al. |
| 2024/0038358 A1 | 2/2024 | Xavier et al. |
| 2024/0071606 A1 | 2/2024 | Xavier et al. |

FOREIGN PATENT DOCUMENTS

| | | |
|---|---|---|
| CA | 2 060 151 | 8/1997 |
| CA | 2 125 300 | 10/1999 |
| CA | 2 630 102 | 10/2008 |
| CA | 2 687 587 | 12/2008 |

(56) References Cited

FOREIGN PATENT DOCUMENTS

| | | |
|---|---|---|
| CA | 2 897 897 | 7/2014 |
| CA | 2 898 825 | 7/2014 |
| CA | 2 900 564 | 10/2014 |
| CA | 2 606 968 | 1/2020 |
| CN | 1759398 | 4/2006 |
| CN | 102521474 | 6/2012 |
| CN | 103816582 | 5/2014 |
| CN | 103920206 | 7/2014 |
| CN | 102300501 | 4/2015 |
| CN | 104487976 | 4/2015 |
| CN | 107810536 | 1/2023 |
| DE | 31 12 762 | 1/1983 |
| DE | 34 35 647 | 7/1985 |
| DE | 198 44 252 | 3/2000 |
| DE | 199 32 147 | 1/2001 |
| DE | 103 52 456 | 7/2005 |
| EP | 0 319 267 | 6/1989 |
| EP | 0 380 061 | 8/1990 |
| EP | 0 384 155 | 8/1990 |
| EP | 0 460 533 | 12/1991 |
| EP | 0 564 127 | 6/1993 |
| EP | 0 633 035 | 1/1995 |
| EP | 0 652 528 | 5/1995 |
| EP | 0 672 427 | 9/1995 |
| EP | 0 683 465 | 11/1995 |
| EP | 0 880 936 | 12/1998 |
| EP | 1050993 A2 * | 11/2000 ............ G06F 21/40 |
| EP | 1 157 711 | 11/2001 |
| EP | 1 174 817 | 1/2002 |
| EP | 0 664 102 | 4/2002 |
| EP | 1 197 178 | 4/2002 |
| EP | 0 830 775 | 8/2002 |
| EP | 1 500 025 | 4/2003 |
| EP | 1 487 171 | 7/2007 |
| EP | 1 933 497 | 6/2008 |
| EP | 2 026 223 | 2/2009 |
| EP | 2 113 842 | 11/2009 |
| EP | 2 228 004 | 9/2010 |
| EP | 2 243 506 | 10/2010 |
| EP | 2 410 448 | 1/2012 |
| EP | 2 742 961 | 6/2014 |
| EP | 2 874 087 | 5/2015 |
| ES | 2 371 995 | 1/2012 |
| FR | 2 717 919 | 9/1995 |
| GB | 2 285 135 | 6/1995 |
| JP | 04-161139 | 6/1992 |
| JP | 07-502678 | 3/1995 |
| JP | 11-500643 | 1/1999 |
| JP | 2000-316820 | 11/2000 |
| JP | 2002-531154 | 9/2002 |
| JP | 2003-016183 | 1/2003 |
| JP | 2003-296173 | 10/2003 |
| JP | 2003-308586 | 10/2003 |
| JP | 2005-021463 | 1/2005 |
| JP | 2005-527284 | 9/2005 |
| JP | 2005-284846 | 10/2005 |
| JP | 2006-047319 | 2/2006 |
| JP | 2006-520949 | 9/2006 |
| JP | 2007-518479 | 7/2007 |
| JP | 2007-525256 | 9/2007 |
| JP | 2008-080036 | 4/2008 |
| JP | 2008-516303 | 5/2008 |
| JP | 2008-158622 | 7/2008 |
| JP | 2008-529675 | 8/2008 |
| JP | 2009-163534 | 7/2009 |
| JP | 2010-502361 | 1/2010 |
| JP | 2011-506048 | 3/2011 |
| JP | 2012-011204 | 1/2012 |
| JP | 2012-070991 | 4/2012 |
| JP | 2012-523895 | 10/2012 |
| JP | 2014-068283 | 4/2014 |
| JP | 5647644 | 1/2015 |
| TW | 200426656 | 12/2004 |
| TW | 1631966 | 8/2018 |
| WO | WO 84/001719 | 5/1984 |
| WO | WO 91/016416 | 10/1991 |
| WO | WO 92/010985 | 7/1992 |
| WO | WO 92/013322 | 8/1992 |
| WO | WO 94/005355 | 3/1994 |
| WO | WO 96/008755 | 3/1996 |
| WO | WO 96/025186 | 8/1996 |
| WO | WO 96/025963 | 8/1996 |
| WO | WO 98/012670 | 3/1998 |
| WO | WO 98/019263 | 5/1998 |
| WO | WO 99/051003 | 10/1999 |
| WO | WO 00/013580 | 3/2000 |
| WO | WO 00/053243 | 9/2000 |
| WO | WO 01/014974 | 3/2001 |
| WO | WO 01/033484 | 5/2001 |
| WO | WO 01/045014 | 6/2001 |
| WO | WO 01/083007 | 11/2001 |
| WO | WO 02/005702 | 1/2002 |
| WO | WO 02/036044 | 5/2002 |
| WO | WO 02/049153 | 6/2002 |
| WO | WO 02/049279 | 6/2002 |
| WO | WO 02/069099 | 9/2002 |
| WO | WO 02/081015 | 10/2002 |
| WO | WO 02/088875 | 11/2002 |
| WO | WO 03/006091 | 1/2003 |
| WO | WO 03/023551 | 3/2003 |
| WO | WO 03/050917 | 6/2003 |
| WO | WO 03/091836 | 11/2003 |
| WO | WO 03/094092 | 11/2003 |
| WO | WO 2004/060455 | 7/2004 |
| WO | WO 2004/070557 | 8/2004 |
| WO | WO 2004/070562 | 8/2004 |
| WO | WO 2004/072828 | 8/2004 |
| WO | WO 2005/036447 | 4/2005 |
| WO | WO 2005/050526 | 6/2005 |
| WO | WO 2005/057175 | 6/2005 |
| WO | WO 2005/066872 | 7/2005 |
| WO | WO 2007/087443 | 8/2007 |
| WO | WO 2007/117705 | 10/2007 |
| WO | WO 2007/127879 | 11/2007 |
| WO | WO 2007/127880 | 11/2007 |
| WO | WO 2008/064254 | 5/2008 |
| WO | WO 2008/067245 | 6/2008 |
| WO | WO 2008/082854 | 7/2008 |
| WO | WO 2008/088490 | 7/2008 |
| WO | WO 2008/097316 | 8/2008 |
| WO | WO 2008/103915 | 8/2008 |
| WO | WO 2008/124478 | 10/2008 |
| WO | WO 2008/134146 | 11/2008 |
| WO | WO 2009/016504 | 2/2009 |
| WO | WO 2009/023406 | 2/2009 |
| WO | WO 2009/023407 | 2/2009 |
| WO | WO 2009/023634 | 2/2009 |
| WO | WO 2009/036327 | 3/2009 |
| WO | WO 2009/049252 | 4/2009 |
| WO | WO 2010/017279 | 2/2010 |
| WO | WO 2010/033919 | 3/2010 |
| WO | WO 2010/053703 | 5/2010 |
| WO | WO 2010/075371 | 7/2010 |
| WO | WO 2010/099313 | 9/2010 |
| WO | WO 2010/114929 | 10/2010 |
| WO | WO 2010/119409 | 10/2010 |
| WO | WO 2010/124127 | 10/2010 |
| WO | WO 2010/130992 | 11/2010 |
| WO | WO 2010/135646 | 11/2010 |
| WO | WO 2010/135654 | 11/2010 |
| WO | WO 2010/135686 | 11/2010 |
| WO | WO 2011/005633 | 1/2011 |
| WO | WO 2011/022549 | 2/2011 |
| WO | WO 2012/048833 | 4/2012 |
| WO | WO 2012/049214 | 4/2012 |
| WO | WO 2012/049218 | 4/2012 |
| WO | WO 2012/120078 | 9/2012 |
| WO | WO 2012/140547 | 10/2012 |
| WO | WO 2012/164556 | 12/2012 |
| WO | WO 2012/170942 | 12/2012 |
| WO | WO 2013/045506 | 4/2013 |
| WO | WO 2014/100736 | 6/2014 |
| WO | WO 2014/131729 | 9/2014 |
| WO | WO 2014/131730 | 9/2014 |

(56) References Cited

FOREIGN PATENT DOCUMENTS

| WO | WO 2015/047595 | 4/2015 |
|----|----------------|--------|
| WO | WO 2015/124569 | 8/2015 |
| WO | WO 2016/179389 | 11/2016 |
| WO | WO 2019/219290 | 11/2019 |
| WO | WO 00/003344 | 1/2020 |
| WO | WO 2020/227403 | 11/2020 |
| WO | WO 2021/201884 | 10/2021 |
| WO | WO 2022/006014 | 1/2022 |
| WO | WO 2022/051230 | 3/2022 |
| WO | WO 2023/159134 | 8/2023 |

OTHER PUBLICATIONS

J. Yoo and J. H. Yi, "Code-Based Authentication Scheme for Lightweight Integrity Checking of Smart Vehicles," in IEEE Access, vol. 6, pp. 46731-46741, 2018, doi: 10.1109/ACCESS.2018. 2866626.*
International Search Report dated Jul. 20, 2020 for International Patent Application No. PCT/US2020/031664, filed May 6, 2020.
Akridge, Jeannie, "New Pumps Outsmart User Error", Healthcare Purchasing News, Apr. 2011, pp. 10, http://web.archive.org/web/20110426122450/http://www.hpnonline.com/inside/2011-04/1104-OR-Pumps.html.
Alur et al., "Formal Specifications and Analysis of the Computer-Assisted Resuscitation Algorithm (CARA) Infusion Pump Control System", International Journal on Software Tools for Technology Transfer, Feb. 2004, vol. 5, No. 4, pp. 308-319.
Aragon, Daleen RN, Ph.D., CCRN, "Evaluation of Nursing Work Effort and Perceptions About Blood Glucose Testing in Tight Glycemic Control", American Journal of Critical Care, Jul. 2006, vol. 15, No. 4, pp. 370-377.
ASHP Advantage, "Improving Medication Safety in Health Systems Through Innovations in Automation Technology", Proceedings of Educational Symposium and Educational Sessions during the 39th ASHP Midyear Clinical Meeting, Dec. 5-9, 2004, Orlando, FL, pp. 28.
Beard et al., "Total Quality Pain Management: History, Background, Resources", Abbott Laboratories, TQPM Survey History, available Feb. 2015 or earlier, pp. 1-3.
Bektas et al., "Bluetooth Communication Employing Antenna Diversity", Proceedings of Eight IEEE International Symposium on Computers and Communication, Jul. 2003, pp. 6.
Bequette, Ph.D., "A Critical Assessment of Algorithms and Challenges in the Development of a Closed-Loop Artificial Pancreas", Diabetes Technology & Therapeutics, Feb. 28, 2005, vol. 7, No. 1, pp. 28-47.
Bequette, B. Wayne, Ph.D., "Analysis of Algorithms for Intensive Care Unit Blood Glucose Control", Journal of Diabetes Science and Technology, Nov. 2007, vol. 1, No. 6, pp. 813-824.
Braun, "Infusomat® Space and Accessories", Instructions for Use, Nov. 2010, pp. 68. http://corp.bbraun.ee/Extranet/Infusioonipumbad/Kasutusjuhendid/Vanad/Kasutusjuhend-Infusomat_Space(vers688J,inglise_k).pdf.
Brownlee, Seth, "Product Spotlight: The Plum A+ with Hospira MedNet Infusion System", PP&P Magazine, Dec. 2005, vol. 2, No. 7, pp. 2.
Cannon, MD et al., "Automated Heparin-Delivery System to Control Activated Partial Thromboplastin Time", Circulation, Feb. 16, 1999, vol. 99, pp. 751-756.
Cardinal Health, "Alaris® Syringe Pumps" Technical Service Manual, Copyright 2002-2006, Issue 9, pp. 1-88, http://www.frankshospitalworkshop.com/equipment/documents/infusion_pumps/service_manuals/Cardinal_Alaris_-_Service_Manual.pdf.
"CareAware® Infusion Management", Cerner Store, as printed May 12, 2011, pp. 3, https://store.cerner.com/items/7.
Chen et al., "Enabling Location-Based Services on Wireless LANs", The 11th IEEE International Conference on Networks, ICON 2003, Sep. 28-Oct. 1, 2003, pp. 567-572.

"Computer Dictionary", Microsoft Press, Third Edition, Microsoft Press, 1997, pp. 430 & 506.
"Context-Free Grammar", Wikipedia.org, as last modified Mar. 5, 2010 in 11 pages, https://en.wikipedia.org/w/index.php/?title=Context-free_grammar&oldid=347915989.
Crawford, Anne J., MSN, RNC, "Building a Successful Quality Pain Service: Using Patient Satisfaction Data and the Clinical Practice Guideline", USA, 1995, pp. 1-6.
Crocker et al., "Augmented BNF for Syntax Specifications: ABNF", Network Working Group, Standards Track, Jan. 2008, pp. 16.
Davidson et al., "A Computer-Directed Intravenous Insulin System Shown to be Safe, Simple, and Effective in 120,618 h of Operation", Diabetes Care, Oct. 2005, vol. 28, No. 10, pp. 2418-2423.
Davies, T., "Cordless Data Acquisition in a Hospital Environment", IEE Colloquium on Cordless Computing—Systems and User Experience, 1993, pp. 4.
Dayhoff et al., "Medical Data Capture and Display: The Importance of Clinicians' Workstation Design", AMIA, Inc., 1994, pp. 541-545.
Diabetes Close Up, Close Concerns AACE Inpatient Management Conference Report, Consensus Development Conference on Inpatient Diabetes and Metabolic Control, Washington, D.C., Dec. 14-16, 2003, pp. 1-32.
"Download", Free On-Line Dictionary of Computing, as archived Jun. 16, 2010 in 1 page, http://web.archive.org/web/20100616010314/https://foldoc.org/download.
East PhD et al., "Digital Electronic Communication Between ICU Ventilators and Computers and Printers", Respiratory Care, Sep. 1992, vol. 37, No. 9, pp. 1113-1122.
Einhorn, George W., "Total Quality Pain Management: A Computerized Quality Assessment Tool for Postoperative Pain Management", Abbott Laboratories, Chicago, IL, Mar. 2, 2000, pp. 1-4.
Eskew et al., "Using Innovative Technologies to Set New Safety Standards for the Infusion of Intravenous Medications", Hospital Pharmacy, 2002, vol. 37, No. 11, pp. 1179-1189.
Felleiter et al., "Data Processing in Prehospital Emergency Medicine", International journal of Clinical Monitoring and Computing, Feb. 1995, vol. 12, No. 1, pp. 37-41.
"File Verification", Wikipedia.org, as last modified Oct. 11, 2011 in 2 pages, https://en.wikipedia.org/w/index.php?title=File_verification&oldid=455048290.
Fogt et al., Development and Evaluation of a Glucose Analyzer for a Glucose-Controlled Insulin Infusion System (Biostator®), Clinical Chemistry, 1978, vol. 24, No. 8, pp. 1366-1372.
Gabel et al., "Camp: A Common API for Measuring Performance", 21st Large Installations System Administration Conference (LISA '07), 2007, pp. 49-61.
Gage et al., "Automated Anesthesia Surgery Medical Record System", International Journal of Clinical Monitoring and Computing, Dec. 1990, vol. 7, No. 4, pp. 259-263.
Galt et al., "Personal Digital Assistant-Based Drug Information Sources: Potential to Improve Medication Safety", Journal of Medical Library Association, Apr. 2005, vol. 93, No. 2, pp. 229-236.
Gardner, Ph.D. et al., "Real Time Data Acquisition: Recommendations for the Medical Information Bus (MIB)", 1992, pp. 813-817.
"General-Purpose Infusion Pumps", Health Devices, EXRI Institute, Oct. 1, 2002, vol. 31, No. 10, pp. 353-387.
Givens et al., "Exploring the Internal State of User Interfaces by Combining Computer Vision Techniques with Grammatical Inference", Proceedings of the 2013 International Conference on Software Engineering, San Francisco, CA, May 18-26, 2013, pp. 1165-1168.
Glaeser, "A Hierarchical Minicomputer System for Continuous Post-Surgical Monitoring", Computers and Biomedical Research, Aug. 31, 1975, pp. 336-361.
Goldberg et al., "Clinical Results of an Updated Insulin Infusion Protocol in Critically Ill Patients", Diabetes Spectrum, 2005, vol. 18, No. 3, pp. 188-191.
Gomez et al., "CLAM: Connection-Less, Lightweight, and Multiway Communication Support for Distributed Computing", Computer Science, 1997, vol. 1199, pp. 227-240.
"GPS Tracker for Medical Equipment", http://www.trackingsystem.com/forbusinesses/corporate-trackingsystem/1098-gps-tracker-formedicalequipment.html, Mar. 15, 2015, pp. 2.

(56) References Cited

OTHER PUBLICATIONS

Graseby, "Model 3000/500 and Micro 3100/505: Volumetric Infusion Pump", Technical Service Manual, Graseby Medical Ltd., Apr. 2002, Issue A, pp. 160.

Graseby, "Model 3000/500 and Micro 3100/505: Volumetric Infusion Pump: Illustrated Parts List for Pump Serial Numbers from 3000 to 59,999", Technical Service Manual, Graseby Medical Ltd., Apr. 2002, Issue A, pp. 71.

Halpern et al., "Changes in Critical Care Beds and Occupancy in the United States 1985-2000: Differences Attributable to Hospital Size", Critical Care Medical, Aug. 2006, vol. 34, No. 8, pp. 2105-2112.

Hamann et al., "PUMPSIM: A Software Package for Simulating Computer-Controlled Drug Infusion Pumps", Annual International Conference of the IEEE Engineering in Medicine and Biology Society, 1990, vol. 12, No. 5, pp. 2019-2020.

Hasegawa et al., "On a Portable Memory Device for Physical Activities and Informations of Maternal Perception", Journal of Perinatal Medicine, 1988, vol. 16, No. 4, pp. 349-356.

Hawley et al., "Clinical Implementation of an Automated Medical Information Bus in an Intensive Care Unit", Proceedings of the Annual Symposium on Computer Application in Medical Care, Nov. 9, 1988, pp. 621-624.

Hayes-Roth et al., "Guardian: A Prototype Intelligent Agent for Intensive-Care Monitoring", Artificial Intelligence in Medicine, vol. 4, Dec. 31, 1992, pp. 165-185.

Hospira, GemStar® Pain Management Infusion System 9-084-PR1-2-2, www.hospira.com/products/gemstar_painmanagement.aspx, Jan. 28, 2010, pp. 1-2.

Introducing Abbott TQPM (Total Quality Pain Management), Abbott Laboratories, Abbott Park, IL, May 2000, pp. 1-4.

"Infusion Pump", Wikipedia.org, as last modified Mar. 27, 2014, in 3 pages, https://web.archive.org/web/20140703024932/https://en.wikipedia.org/wiki/Infusion_pump.

Isaka et al., "Control Strategies for Arterial Blood Pressure Regulation", IEEE Transactions on Biomedical Engineering, Apr. 1993, vol. 40, No. 4, pp. 353-363.

Johnson et al., "Using BCMA Software to Improve Patient Safety in Veterans Administration Medical Centers", Journal of Healthcare Information Management, Dec. 6, 2004, vol. 16, No. 1, pp. 46-51.

Kent Displays, "Reflex™ Electronic Skins", Product Brief 25127B, 2009, pp. 2.

Kent Displays, "Reflex Electronic Skins Engineering Evaluation Kit", 25136A, Mar. 10, 2009.

Lefkowitz et al., "A Trial of the Use of Bar Code Technology to Restructure a Drug Distribution and Administration System", Hospital Pharmacy, Mar. 31, 1991, vol. 26, No. 3, pp. 239-242.

Lenssen et al., "Bright Color Electronic Paper Technology and Applications", IDS '09 Publication EP1-2 (Phillips Research), 2009, pp. 529-532.

Leveson, Nancy, "Medical Devices: The Therac-25", Appendix A, University of Washington, 1995, pp. 49.

Linkens, D.A. "Computer Control for Patient Care", Computer Control of Real-Time Processes, IEE Control Engineering Series 41, 1990, Ch. 13, pp. 216-238.

Mako Hill et al., "The Official Ubuntu Book", Shoeisha Co., Ltd., 1st Edition, Jun. 11, 2007, pp. 115 to 125.

Marshall, et al., "New Microprocessor-Based Insulin Controller", IEEE Transactions on Biomedical Engineering, Nov. 1983, vol. BME-30, No. 11, pp. 689-695.

Martino et al., "Automation of a Medical Intensive Care Environment with a Flexible Configuration of Computer Systems", Proceedings of the Annual Symposium on Computer Application in Medical Care, Nov. 5, 1980, vol. 3, pp. 1562-1568.

Matsunaga et al., "On the Use of Machine Learning to Predict the Time and Resources Consumed by Applications", 2010 10th IEEE/ACM International Conference on Cluster, Cloud and Grid Computing (CCGrid), May 17-20, 2010, pp. 495-504.

Mauseth et al., "Proposed Clinical Application for Tuning Fuzzy Logic Controller of Artificial Pancreas Utilizing a Personalization Factor", Journal of Diabetes Science and Technology, Jul. 2010, vol. 4, No. 4, pp. 913-922.

Medfusion™, "Medfusion Syringe Infusion Pump Model 4000", Operator's Manual, Software Version V1.1, Sep. 2011, pp. 154. http://www.medfusionpump.com/assets/literature/manuals/Operators_Manual_4000_40-5760-51A.pdf.

Metnitz et al., "Computer Assisted Data Analysis in Intensive Care: the ICDEV Project-Development of a Scientific Database System for Intensive Care", International Journal of Clinical Monitoring and Computing, Aug. 1995, vol. 12, No. 3, pp. 147-159.

Micrel Medical Devices, "MP Daily +" http://web.archive.org/web/20130803235715/http://www.micrelmed.com/index.aspx?productid=9 as archived Aug. 3, 2013 in 1 page.

Moghissi, Etie, MD, FACP, FACE, "Hyperglycemia in Hospitalized Patients", A Supplement to ACP Hospitalist, Jun. 15, 2008, pp. 32.

Murray, Jr. et al., "Automated Drug Identification System (during surgery)", IEEE Proceedings of Southeastcon '91, Apr. 7-10, 1991, pp. 265.

Nicholson et al., "'Smart' Infusion Apparatus for Computation and Automated Delivery of Loading, Tapering, and Maintenance Infusion Regimens of Lidocaine, Procainamide, and Theophylline", Proceedings of The Seventh Annual Symposium on Computer Applications in Medical Care, Oct. 1983, pp. 212-213.

Nolan et al., "The P1073 Medical Information Bus Standard: Overview and Benefits for Clinical Users", 1990, pp. 216-219.

Omnilink Systems, Inc., "Portable Medical Equipment Tracking", http://www.omnilink.com/portablemedicalequipmenttracking/, Mar. 15, 2015, pp. 2.

O'Shea, Kristen L., "Infusion Management: Working Smarter, Not Harder", Hospital Pharmacy, Apr. 2013, vol. 48, No. 3, pp. S1-S14.

Package Management in Debian GNU/Linux, Debian GNU/Linux Expert Desktop Use Special, Giutsu-Hyohron Co., Ltd., First Edition, Sep. 25, 2004, pp. 183-185.

Passos et al., "Distributed Software Platform for Automation and Control of General Anaesthesia", Eighth International Symposium on Parallel and Distributed Computing, ISPDC '09, Jun. 30-Jul. 4, 2009, pp. 8.

Philips, "IntelliSpace Event Management and IntelliVue Patient Monitoring", Release 10, 2011, http://incenter.medical.philips.com/doclib/enc/fetch/2000/4504/577242/577243/577247/582646/583147/8359175/Philips_Patient_Monitoring_and_IntelliSpace_Event_Management_Interoperability.pdf%3fnodeid%3d8508574%26vernum%3d-2, pp. 2.

Pretty et al., "Hypoglycemia Detection in Critical Care Using Continuous Glucose Monitors: An in Silico Proof of Concept Analysis", Journal of Diabetes Science and Technology, Jan. 2010, vol. 4, No. 1, pp. 15-24.

Rappoport, Arthur E., "A Hospital Patient and Laboratory machine-Readable Identification System (MRIS) Revisited", Journal of Medical Systems, Apr. 1984, vol. 8, Nos. 1/2, pp. 133-156.

Ritchie et al., "A Microcomputer Based Controller for Neuromuscular Block During Surgery", Annals of Biomedical Engineering, Jan. 1985, vol. 13, No. 1, pp. 3-15.

Saager et al., "Computer-Guided Versus Standard Protocol for Insulin Administration in Diabetic Patients Undergoing Cardiac Surgery", Annual Meeting of the American Society of Critical Care Anesthesiologists, Oct. 13, 2006.

Sanders et al., "The Computer in a Programmable Implantable Medication System (PIMS)", Proceedings of the Annual Symposium on Computer Application in Medical Care, Nov. 2, 1982, pp. 682-685.

Schilling et al., "Optimizing Outcomes! Error Prevention and Evidence-Based Practice with IV Medications", A Pro-Ce Publication, Hospira, Inc., Feb. 6, 2012, pp. 56.

Schulze et al., "Advanced Sensors Technology Survey", Final Report, Feb. 10, 1992, pp. 161.

Scott, et al., "Using Bar-Code Technology to Capture Clinical Intervention Data in a Hospital with a Stand-Alone Pharmacy Computer System", Mar. 15, 1996, American Journal of Health-System Pharmacy, vol. 53, No. 6, pp. 651-654.

(56) References Cited

OTHER PUBLICATIONS

Sebald et al., "Numerical Analysis of a Comprehensive in Silico Subcutaneous Insulin Absorption Compartmental Model", 31st Annual International Conference of the IEEE Engineering in Medicine and Biology Society, Sep. 2-6, 2009, pp. 3901-3904.
Shabot, M. Michael, "Standardized Acquisition of Bedside Data: The IEEE P1073 Medical Information Bus", International Journal of Clinical Monitoring and Computing, vol. 6, Sep. 27, 1989, pp. 197-204.
Sheppard, Louis, Ph.D., "Automation of the Infusion of Drugs Using Feedback Control", Journal of Cardiothoracic and Vascular Anesthesia, Feb. 28, 1989, vol. 3, No. 1, pp. 1-3.
Sheppard, Louis, Ph.D., "Computer Control of the Infusion of Vasoactive Drugs", Annals of Biomedical Engineering, Jul. 1980, vol. 8, No. 4-6, pp. 431-444.
Sheppard, Louis, Ph.D., "The Application of Computers to the Measurement, Analysis, and Treatment of Patients Following Cardiac Surgical Procedures", The University of Alabama in Birmingham, Oct. 31, 1977, pp. 297-300.
Sheppard, Louis, Ph.D., "The Computer in the Care of Critically Ill Patients", Proceedings of the IEEE, Sep. 1979, vol. 67, No. 9, pp. 1300-1306.
"Sigma Spectrum: Operator's Manual", Oct. 2009, pp. 72. http://static.medonecapital.com/manuals/userManuals/Sigma-Spectrum-Operator-Manual-October-2009.pdf.
Simonsen, Michael Ph.D., POC Testing, New Monitoring Strategies on Fast Growth Paths in European Healthcare Arenas, Biomedical Business & Technology, Jan. 2007, vol. 30, No. 1, pp. 1-36.
Siv-Lee et al., "Implementation of Wireless 'Intelligent' Pump IV Infusion Technology in a Not-for-Profit Academic Hospital Setting", Hospital Pharmacy, Sep. 2007, vol. 42, No. 9, pp. 832-840. http://www.thomasland.com/hpj4209-832.pdf.
Slack, W.V., "Information Technologies for Transforming Health Care", https://www.andrew.cmu.edu/course/90-853/medis.dir/otadocs.dir/03ch2.pdf, Ch. 2, 1995, pp. 29-78.
Smith, Joe, "Infusion Pump Informatics", CatalyzeCare: Transforming Healthcare, as printed May 12, 2011, pp. 2.
Sodders, Lisa, "VA Center Keeps Medicine in Right Hands", The Capital—Journal, Dec. 4, 1999, pp. 1-2.
"Software Versioning", Wikipedia.org, dated Oct. 16, 2011 in 11 pages, https://en.wikipedia.org/w/index.php?title=Software_versioning&oldid=455859110.
Stitt, F.W., "The Problem-Oriented Medical Synopsis: a Patient-Centered Clinical Information System", Proceedings of the Annual Symposium on Computer Application in Medical Care, 1994, pp. 88-92.
Stokowski, Laura A. RN, MS, "Using Technology to Improve Medication Safety in the Newborn Intensive Care Unit", Advances in Neonatal Care, Dec. 2001, vol. 1, No. 2, pp. 70-83.
Sutton et al., "The Syntax and Semantics of the PROforma Guideline Modeling Language", Journal of the American Medical Informatics Association, Sep./Oct. 2003, vol. 10, No. 5, pp. 433-443.
Szeinbach et al., "Automated Dispensing Technologies: Effect on Managed Care", Journal of Managed Care Pharmacy (JMCP), Sep./Oct. 1995, vol. 1, No. 2, pp. 121-127.
Szolovits et al., "Guardian Angel: Patient-Centered Health Information Systems", Technical Report MIT/LCS/TR-604, Massachusetts Institute of Technology Laboratory for Computer Science, May 1994, pp. 39.
Van Den Berghe, M.D., Ph.D., et al., "Intensive Insulin Therapy in Critically Ill Patients", The New England Journal of Medicine, Nov. 8, 2001, vol. 345, No. 19, pp. 1359-1367.
Van Den Berghe, M.D., Ph.D., et al., "Intensive Insulin Therapy in the Medical ICU", The New England Journal of Medicine, Feb. 2, 2006, vol. 354, No. 5, pp. 449-461.

Van Der Maas et al., "Requirements for Medical Modeling Languages", Journal of the American Medical Informatics Association, Mar./Apr. 2001, vol. 8, No. 2, pp. 146-162.
Villalobos et al., "Computerized System in Intensive Care medicine", Medical Informatics, vol. 11, No. 3, 1986, pp. 269-275.
Wilkins et al., "A Regular Language: The Annotated Case Report Form", PPD Inc., PharmaSUG2011—Paper CD18, 2011, pp. 1-9.
Ying et al., "Regulating Mean Arterial Pressure in Postsurgical Cardiac Patients. A Fuzzy Logic System to Control Administration of Sodium Nitroprusside", IEEE Engineering in Medicine and Biology Magazine, vol. 13, No. 5, Nov.-Dec. 1994, pp. 671-677.
Yue, Ying Kwan, "A Healthcare Failure Mode and Effect Analysis on the Safety of Secondary Infusions", Thesis, Institute of Biomaterials and Biomedical Engineering, University of Toronto, 2012, pp. 168.
Yurkonis et al., "Computer Simulation of Adaptive Drug Infusion", IEEE Transactions on Biomedical Engineering, vol. BME-34, No. 8, Aug. 1987, pp. 633-635.
Zakariah et al., "Combination of Biphasic Transmittance Waveform with Blood Procalcitonin Levels for Diagnosis of Sepsis in Acutely Ill Patients", Critical Care Medicine, 2008, vol. 36, No. 5, pp. 1507-1512.
Ahn et al., "Towards Scalable Authentication in Health Services", Eleventh IEEE International Workshops on Enabling Technologies: Infrastructure for Collaborative Enterprises, Jun. 2002, pp. 83-88.
Bellare et al., "Security Proofs for Identity-Based Identification and Signature Schemes", Lecture Notes in Computer Science, Jan. 2009, vol. 22, No. 1, pp. 18.
Block, Alexander, "Secret Sharing and 1-11 Threshold Signatures with BLS", Jul. 2, 2018, https://blog.dash.org/secret-sharing-and-threshold-signatures-with-bls-954d1587b5f, in 8 pages.
Doesburg et al., "Improved Usability of a Multi-Infusion Setup Using a Centralized Control Interface: A Task-Based Usability Test", Aug. 11, 2017, PLoS ONE, vol. 12, No. 8, pp. 10.
Edworthy, Judy, "Medical Audible Alarms: A Review", Journal of the American Medical Informatics Association, vol. 20, No. 3, 2013, pp. 584-589.
Gutwin et al., "Gone But Not Forgotten: Designing for Disconnection in Synchronous Groupware", CSCW 2010, Feb. 6-10, 2010, Savannah, Georgia, USA., pp. 179-188.
Huang et al., "Secure Identity-Based Data Sharing and Profile Matching for Mobile Healthcare Social Networks in Cloud Computing", vol. 6, Jul. 2018, pp. 36584-36594.
Li et al., "Hijacking an Insulin Pump: Security Attacks and Defenses for a Diabetes Therapy System", 2011 IEEE 13th International Conference on e-Health Networking, Applications and Services, 2011, pp. 150-156.
"McKesson Automation and ALARIS Medical Systems Developing Point-of-Care Bar Coding Solution to Improve IV Medication Safety", PR Newswire, NY, Dec. 9, 2002, pp. 4.
Michienzi, Kelly, "Managing Drug Library Updates", Pharmacy Purchasing Products, https://www.pppmag.com/article/1061, Feb. 2012, vol. 9, pp. 22-23.
"Sigma Spectrum: Operator's Manual", May 15, 2008, pp. 63. <https://usme.com/content/manuals/sigma-spectrum-operator-manual.pdf>.
Solapurkar et al., "Building Secure Healthcare Services Using OAuth 2.0 and JSON Web Token in IOT Cloud Scenario", Dec. 2016, 2nd International Conference on Contemporary Computing and Informatics, pp. 99-10.
"TCG TPM v2.0 Provisioning Guidance", Reference, Version 1, Revision 1, Mar. 15, 2017, pp. 1-43.
Murphy, Robert, "The Design of Safety-Critical Medical Infusion Devices", May 30, 2007, Doctor of Philosophy submission, pp. 317.
Rahmani et al., "Smart e-Health Gateway: Bringing Intelligence to Internet-of-Things Based Ubiquitous Healthcare Systems", 2015 12th Annual IEEE Consumer Communications and Networking Conference (CCNC), Jul. 2015, pp. 826-834.

\* cited by examiner

THRESHOLD SIGNATURE BASED MEDICAL DEVICE MANAGEMENT

CROSS-REFERENCE TO RELATED APPLICATIONS

The present application is a continuation of International Patent Application No. PCT/US2020/031664, filed on May 6, 2020 and titled "Threshold Signature Based Medical Device Management," which claims priority to U.S. Provisional Patent Application No. 62/845,115, filed on May 8, 2019 and titled "Threshold Signature Based Medical Device Management," the contents of both of which are incorporated by reference herein.

TECHNICAL FIELD

This disclosure relates to the field of medical device management, and particularly to systems and methods for secure authorization of medical devices.

BACKGROUND

Computing systems, such as medical devices that have processors and other computing components, execute software that controls the functions performed by the computing systems. Software is typically stored in a persistent data store (e.g., hard disk, flash memory, etc.), and loaded into volatile memory (e.g., random access memory or RAM) for execution. Computing systems often verify whether software is authorized prior to execution. For example, the computing system may determine whether a license has been obtained, authorizing execution of the software. If a valid license has been obtained, then execution of the software may be permitted. If no license has been obtained, then execution of the software may be blocked.

SUMMARY

Various techniques for managing the operation of devices using threshold signature-based authorization are described herein. These techniques may include creating shares of digital signature generation keys, and assigning the shares to devices or individual components of devices. The shares may then be used to authorize performance of particular functions so long as a threshold number of shares—or a threshold amount of weighted shares—are available during the authorization procedure. For example, threshold signature-based authorization may be used to validate licenses, validate the presence of certain components, respond to security events, ensure devices are being used in the intended environment, etc. These and other embodiments are described in greater detail below with reference to FIGS. 1-6. Although many of the examples are described in the context of medical devices, functions, and environments (including infusion pumps, medication dispensing functions, and hospital or clinical environments), the techniques described herein can be applied to other types of devices, functions, and environments.

BRIEF DESCRIPTION OF DRAWINGS

Throughout the drawings, reference numbers may be re-used to indicate correspondence between referenced elements. The drawings are provided to illustrate example embodiments described herein and are not intended to limit the scope of the disclosure.

DETAILED DESCRIPTION OF ILLUSTRATIVE EMBODIMENTS

Figure 1:
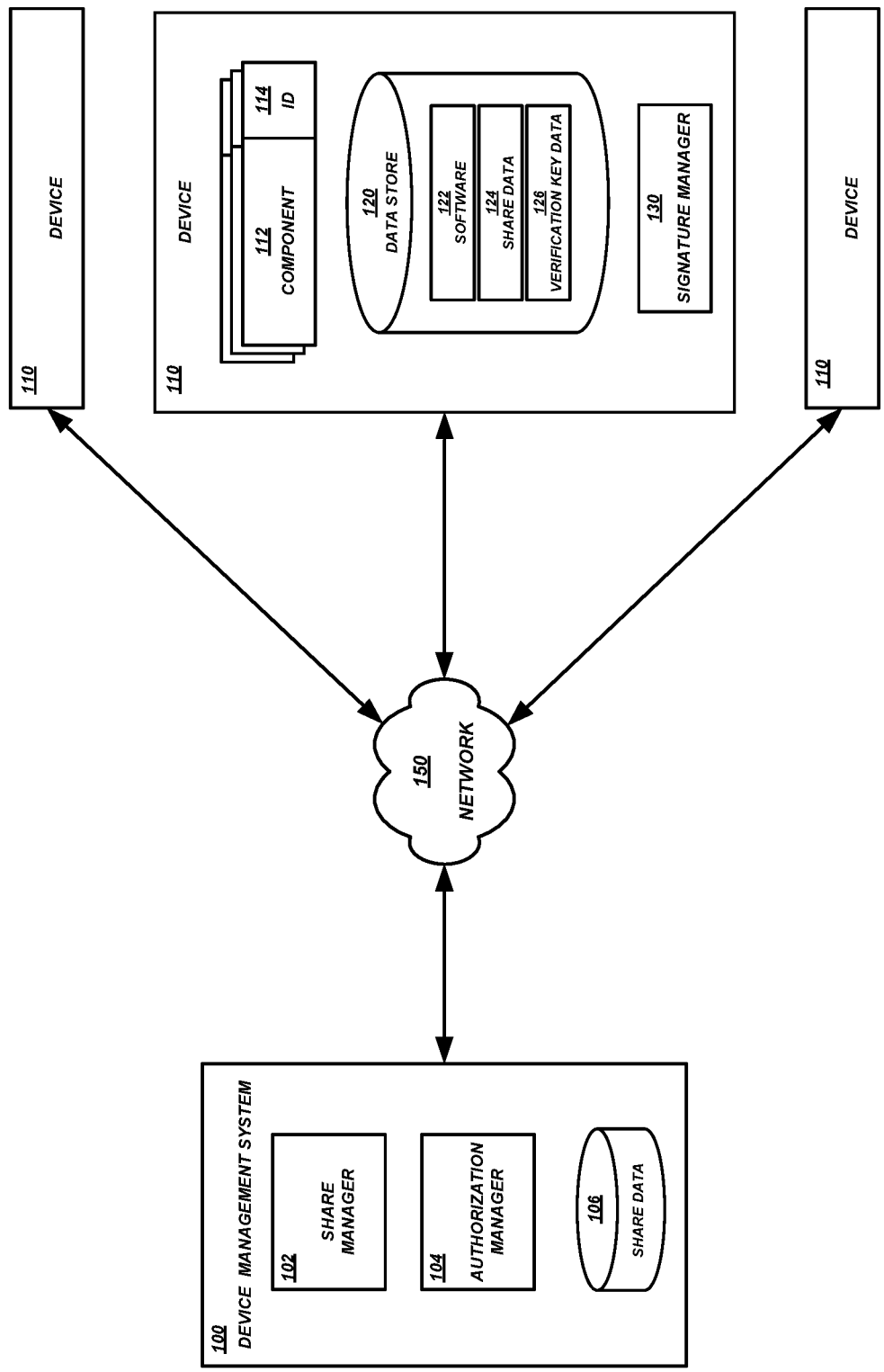
FIG. 1 is a block diagram of an example network environment including a device management system and various devices according to some embodiments.

The present disclosure is directed to managing device authorization through the use of digital signature thresholds. Individual components of a device, or individual devices in a network environment, are associated with separate shares of data from which a digital signature can be generated. For example, the shares of data may be used to generate shares of a digital signature, and the digital signature may be used to authorize performance of a function. The shares of data may be referred to as "secret shares," or simply as "shares" for convenience. In an illustrative embodiment, a threshold number of secret shares are required in order to perform any private operation such as generating a digital signature, recovering secret data, etc. Therefore, an authorization process that relies on digital signature verification to determine that a function is authorized will only do so if a threshold number of secret shares are available at authorization time. If fewer than the threshold number of secret shares are available, then the requested function (or operation of the device as a whole) is blocked. In this way, a device can be required to maintain a threshold number of original or authorized components to continue using licensed software or to continue executing at all. In a similar manner, a device can be prohibited from operation unless a threshold number of connected devices participate in an authorization procedure, or a threshold number of components of the device participate in an authorization procedure.

Some aspects of the present disclosure relate to generating secret shares for individual components of a medical device (e.g., an infusion pump), and using the secret shares to determine whether to authorize a function of the medical device. In some embodiments, software may be installed on a medical device, and a valid license may be required in order to execute the software. During installation or initial licensing, the license may be tied to the current configuration of the medical device such that the software is only permitted to execute if at least a threshold number of components of the medical device remain the same. To enforce this licensing requirement, a different secret share can be assigned to various individual components of the device. For example, there may be n secret shares of such data generated, one for each of n different components of the device. When the software is to execute, an authorization procedure can be performed. An illustrative authorization procedure may involve: (1) generating a different portion or "signature share" of a digital signature using the same message and each of the secret shares associated with device components that are still present; (2) generating a digital signature using the signature shares; and (3) verifying the authenticity of the digital signature (e.g., verifying that the digital signature was generated using a threshold number of secret shares and the message). However, a valid digital signature may only be generated if there are at least a threshold number t of secret shares available at authorization time, where 0<t<n. If too many components have changed or been removed, then fewer than t secret shares may be obtained, a valid digital signature may not be generated, and the verification of the digital signature will fail. In this way, a medical device may be prevented from executing the software (or otherwise performing a now-unauthorized function) if the software has been copied onto a different device, or if some other event has occurred (e.g., the software may no longer be compatible with the medical device in the device's current configuration).

Additional aspects of the present disclosure relate to treating some device components differently than other device components during an authorization process. The mechanism by which the components are treated differently may be the use of weighting factors that are assigned to the components. The weighting factors may also be referred to simply as "weights" for convenience. In some embodiments, a particular component or subset of components may be determined to be more important than other components. The more important components may be assigned a higher weight than less important components. When an authorization process is subsequently performed, the various secret shares and weights associated with the device components currently available to the medical device may be obtained. In generating a digital signature from the weights and secret shares, a threshold amount of weighted secret shares may be required in order to generate a valid digital signature. For example, if relatively important component is not present but all other components are present, the authorization procedure will fail. However, if a comparatively less important component is not present but all other components are present, the authorization procedure may complete successfully. In this way, a medical device may be prevented from operating with too many replacements of critical components, critical replacement components that are not of the correct type, too few original or authorized versions of critical components, etc. Such limitations can improve safety and reliability. In some embodiments, the different components may be assigned different numbers of shares, rather than weights with different values, to indicate the relative importance of the components.

Further aspects of the present disclosure relate to group-based authorization of individual medical devices in a network environment. Group-based authorization may also be referred to as "swarm authentication." In some embodiments, a medical device that is attempting to perform a particular function (e.g., connect to a network server or dispense medication) may be prohibited from doing so unless a threshold number of other medical devices are able to participate in the authorization. This can prevent malicious or otherwise undesirable use of a medical device that may be lost or stolen, because the medical device may not be operating in a network environment (e.g., a hospital or clinic) in which a threshold number of other devices are available to participate in the authorization procedure. For example, each medical device may be provided with or otherwise assigned a secret share. When a particular device attempts to perform a function that requires authorization, a network server can determine which other devices are connected to the network server, and obtain or otherwise access the secret shares for each of the available devices. If a threshold number of secret shares are available, a valid digital signature may be successfully generated, the digital signature may be successfully verified, and the device may then be authorized to perform the function. Otherwise, the device may be blocked from performing the function. Therefore, a medical device that has become lost or stolen may be prevented from operating because it may not be able to connect to the correct clinical network and the group-based authorization process may not be able to obtain the threshold number of secret shares.

Still further aspects of the present disclosure relate to system-wide participation in security authorization. A multi-component system, such as a medical device, may implement dynamically-weighted threshold-based authorization to authorize performance of particular functions (or operation of the device at all). For example, individual components of system may be assigned a starting weight or number of secret shares. As an individual component detects security events (e.g., invalid login attempts, system security override attempts, etc.), the component can dynamically lower the weight that it contributes to system-wide authorization. Other components may perform in a similar manner. When the system attempts to authorize performance of a particular function, a threshold number of weighted secret shares may be required in order to generate a valid digital signature and successfully authorize the function. If a threshold amount of weighted secret shares are not available due to dynamically lowered weights, the authorization process will fail. In this way, individual components of a system can actively participate in the authorization determinations made by the system, even if some components do not otherwise perform security functions.

Although aspects of some embodiments described in the disclosure will focus, for the purpose of illustration, on particular examples of devices, cryptographic secrets, threshold-based authorization algorithms, and the like, the examples are illustrative only and are not intended to be limiting. In some embodiments, the systems and methods described herein may be applied to additional or alternative devices, cryptographic secrets, threshold-based authorization algorithms, etc. Various aspects of the disclosure will now be described with regard to certain examples and embodiments, which are intended to illustrate but not limit the disclosure.

Overview of Example Network Environment

FIG. 1 illustrates network environment in which a device management system 100 communicates with one or more devices 110 via a communication network 150. Illustratively, the environment may include one or more healthcare facilities (e.g., hospitals) in which the devices 110 are medical devices and the device management system 100 is (or is part of) a locally-hosted or cloud-based system to manage use of the medical devices.

In some embodiments, a communication network 150 (also referred to simply as a "network") may be a publicly-accessible network of linked networks, possibly operated by various distinct parties, such as the Internet. In some cases, the network 150 may be or include a private network, personal area network, local area network, wide area network, global area network, cable network, satellite network, cellular data network, etc., or a combination thereof, some or all of which may or may not have access to and/or from the Internet.

The device management system 100 may be a logical association of one or more computing devices for managing the generation and distribution of shares, performance of authorization procedures, and the like. For example, the device management system 100 can include one or more share managers 102. A share manager 102 may correspond to one or more server computing devices for generating secret shares and distributing the secret shares to the various devices 110 that use them. In some embodiments, the secret shares may also or alternatively be stored in a data store 106 corresponding to one or more data storage devices. The device management system 100 may also include one or more authorization managers 104. An authorization manager 104 may correspond to one or more computing devices configured to perform authorization procedures using the secret shares generated by the share manager 102.

In some embodiments, the features and services provided by the device management system 100 may be implemented as web services consumable via one or more communication networks. In further embodiments, the device management system 100 and/or individual components thereof may be provided by one or more virtual machines implemented in a hosted computing environment. The hosted computing environment may include one or more rapidly provisioned and released computing resources, such as computing devices, networking devices, and/or storage devices. A hosted computing environment may also be referred to as a "cloud" computing environment.

The devices 110 may correspond to any of a variety of devices that utilize or are subject to threshold-based authorization. Individual devices 110 may include various components 112, such as processors, network interface cards, volatile memory, long term storage, displays, and the like. Some or all of the components 112 may be associated with corresponding identifiers 114. For example, a processor component 112 may have a unique serial number that serves as the corresponding identifier 114. A memory component 112 may be associated with a different unique serial number that services as the corresponding identifier 114. A long-term storage component 112 (such as a disk drive) may be associated with its own unique serial number that serves as the corresponding identifier 114. In some embodiments, a component with a corresponding identifier may be a software component. For example, an operating system 122 may be stored in a data store 120 (such as a disk drive). The operating system 122 may be associated with its own unique identifier, as with the other components 112, and may therefore be treated similar to the other components 112 (e.g., assigned shares, weights, etc.). The data store 120 may be associated with its own unique identifier, as with the other components 112.

The devices 110 may also include components for performing secret share processing and/or authorization processes. In some embodiments, a device 110 may include a signature manager 130. The signature manager 130 may be a hardware-based component, or a software-based application or subsystem that runs on a processor of the device 110. The signature manager 130 may perform certain secret share processing and authorization processes, as described in greater detail below. For example, the signature manager 130 may access share data 124 and a verification key data 126 from the data store 120 for use in secret share processing and authorization processes. In some embodiments, the share data 124 and/or verification key data 126 may be stored in signature manager 130 or in some other secure location separate from the data store 120.

In some embodiments, the devices 110 may be or include medical devices, such as infusion pumps, with various components 112. For example, an infusion pump may include a motor controller unit ("MCU") configured to control the motor that dispenses medication, a communications engine ("CE") configured to manage network communications to/from the pump, operational software, and various other infusion pump-specific or medical-device specific components, any or all of which may be associated with respective identifiers 114. In addition, the devices 110 themselves may include different types of certain devices, such as different types of infusion pumps. Each type of infusion pump and even different versions of the same type of infusion pump may operate with a different operating system, use a different type of MCU and/or CE, etc.

Secret Share Generation and Distribution Process

Figure 2:
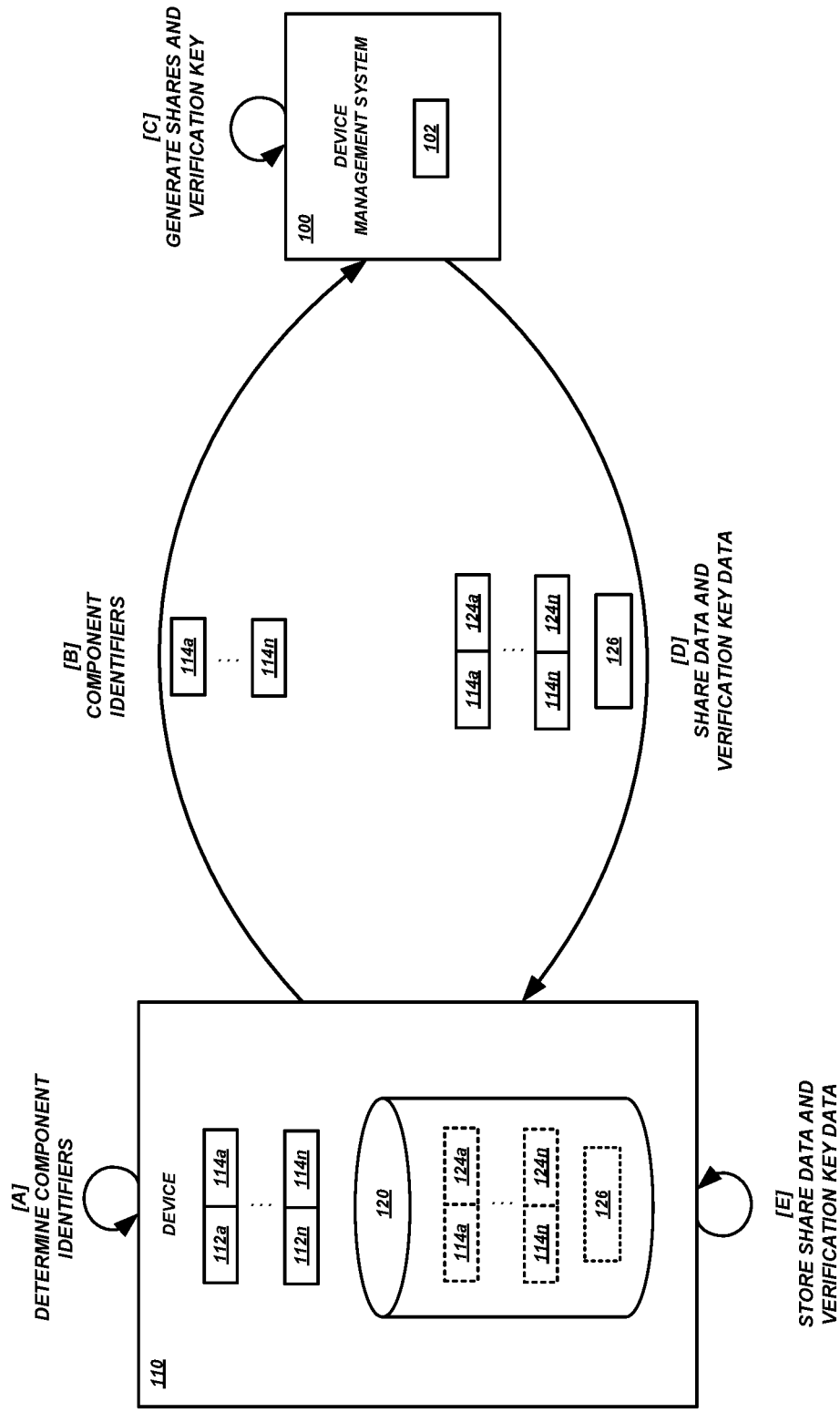
FIG. 2 is a block diagram illustrating data flows and interactions between a device and a device management system during pre-authorization setup according to some embodiments.

FIG. 2 is a block diagram of illustrative data flows and interactions between a device 110 and a device management system 100 during pre-authorization setup. The displayed interactions may occur during installation or initial licensing of software (or some other component). For example, software may be installed on the device 110. In order to verify that the software is licensed for use on the device 110, the software may perform (or cause to be performed) an authorization process that only authorizes execution of the software if a threshold number of components $112a \ldots 112n$ that were present on the device 110 during software installation are still present on the device. In order to facilitate this authorization process, a set of secret, shares for digital signature generation may be obtained, assigned to the components $112a \ldots 112n$, and stored on the device 110. In some embodiments, the secret shares may each be a private encryption key or other key for use with a cryptographic function.

At [A], the device 110 can determine identifiers for a set of n components of the device 110. The value of n may depend on the software being installed, the number of components 112 present in the device 110, requirements of the software, etc. For example, n may be 4, and the set of n components may include a processor, memory, network interface, and battery. Each of the components may have an identifier with which they are already associated (e.g., a serial number). In some embodiments, components may be assigned identifiers as part of the pre-authorization setup. The identifiers may be globally-unique identifiers, or identifiers that are unique for at least the type of component to which they are assigned (e.g., identifiers that, in combination with other data such as model numbers, provide substantially unique identification of the respective components).

At [13], the device 110 can send the identifiers to the device management system 100. For example, the device 110 may transmit the identifiers serially, asynchronously, or in a hatch to the device management system 100.

At [C], the share manager 102 or some other module or component of the device management system 100 generates secret shares, such as individual digital signature share generation keys. A different secret share may be generated for each of the n component identifiers that have been received. The secret shares may be generated such that at least a threshold number t (where $n >= t > 0$) of the secret shares must be available in order to generate a digital signature and proceed with an authorization process. The share manager 102 may also generate a verification key that is used during the authorization process to verify a digital signature generated using signature shares that have been generated using the secret shares.

In some embodiments, secret shares may be generated using Lagrange interpolation and Shamir's secret sharing to determine a random polynomial function from which the secret shares are generated. The different secret shares may correspond to values of the polynomial function for different input values (e.g., $x_1, x_2, \ldots, x_n$). The digital signature generation key may correspond to a value of the polynomial function for a particular predetermined input value (e.g., $x=0$). At authorization time, if at least t secret shares are available (corresponding to at least t different values of the polynomial function for t different input values), then the polynomial function itself may be derived from the secret shares without any other prior knowledge of the polynomial function. The polynomial function may then be evaluated for the predetermined input value that is used to determine the digital signature generation key. If the digital signature generation key is correct, then a digital signature generated using the key will be verified using the verification key that is generated by the share manager 102. If at least t different secret shares are not available, then it may be impossible or computationally infeasible to determine the polynomial function or to otherwise derive the correct digital signature generation key. For example, if there are t−1 shares available, then there may be an infinite number of possible polynomial functions that could be derived from the shares.

The example generation of secret shares described herein is illustrative only, and is not intended to be exhaustive or limiting. In some embodiments, other methods for generating secret shares may be used, such as verifiable secret sharing, Blakely's secret sharing, and the like. Example secret sharing schemes are described in "Secret-Sharing Schemes: A Survey" by Amos Beimel, and "How to Share a Secret" by Adi Shamir, the contents of both of which are incorporated by reference herein and made part of this specification.

At [D], the share manager 102 or some other module or component of the device management system 100 can send share data representing the secret shares, and verification key data representing the verification key, to the device 110. For example, the share manager 102 may transmit the share data and verification key data serially, asynchronously, or in a batch to the device 110.

At [E], the device 110 can store the share data and the verification key data. For example, share data 124a . . . 124n representing secret shares associated with corresponding identifiers 114a . . . 114n, and verification key data 126 representing the verification key, may be stored in the data store 120. In some embodiments, the signature manager 130 may store the share data 124 and verification key data 126 in a secure manner. For example, the share data 124 may be stored such that it is inaccessible outside of the signature manager 130, or such that individual shares are only accessible by querying the signature manager 130 with a valid identifier.

Once the secret shares and verification key have been generated and stored, the device 110 may be ready to execute an authorization process to authorize execution of a particular function such as execution of licensed software.

Threshold-Based Authorization Process

Figure 3:
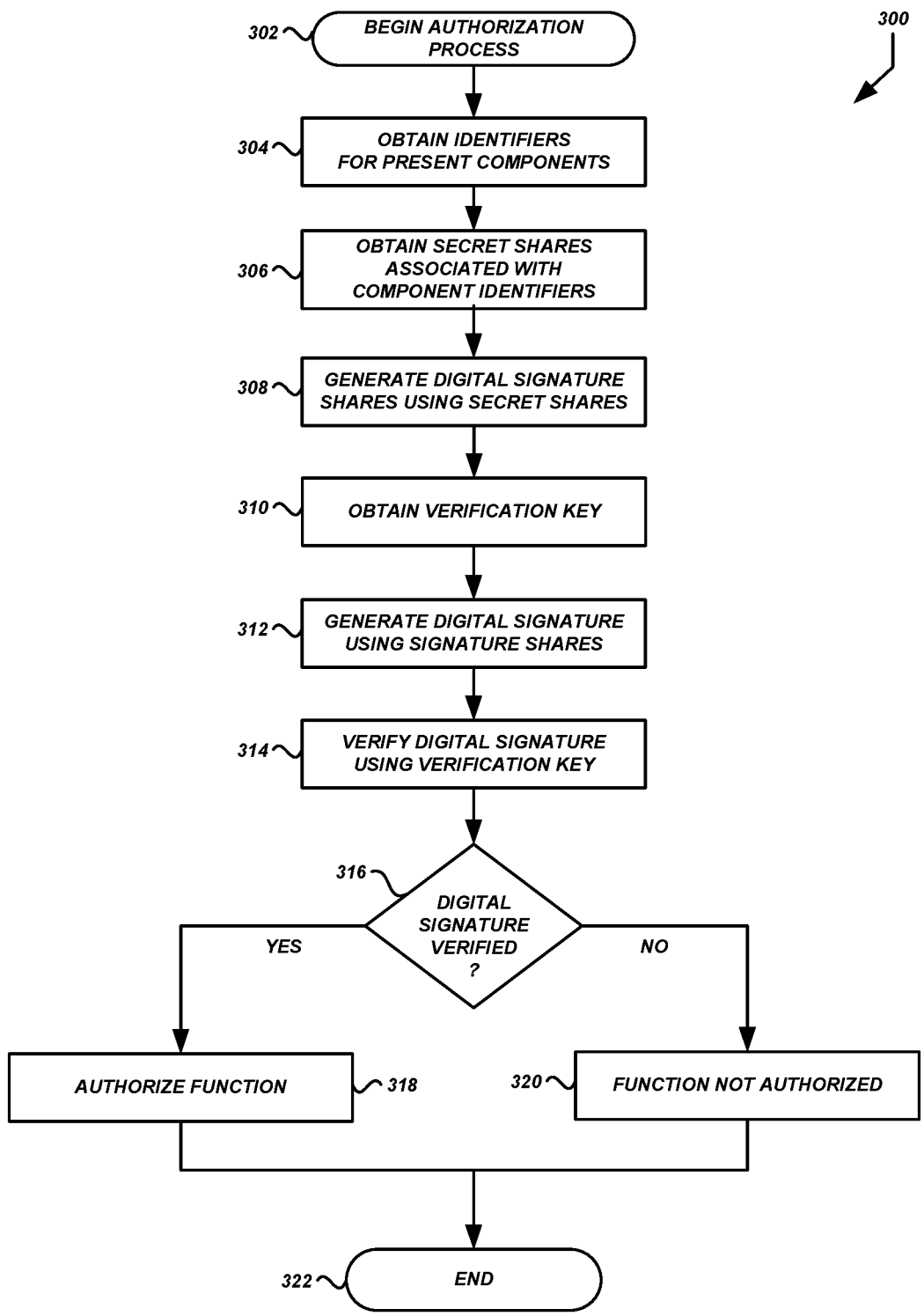
FIG. 3 is a flow diagram of an illustrative process for threshold signature authorization of a device according to some embodiments.

FIG. 3 is a flow diagram of an illustrative process 300 that may be executed by a signature manager 130 or some other component to determine whether a particular function is authorized. Advantageously, the process 300 can authorize the function if a threshold number t of secret shares are able to be obtained, corresponding to a threshold number t of components that were part of the device 110 when the pre-authorization setup process was performed. Otherwise, the process 300 cannot authorize the function if a threshold number t of secret shares are not able to be obtained. In this way, the authorization process can ensure that an authorized function is tied to a threshold number of components, and that the function (e.g., execution of software) will not be authorized if the software is installed on a different device 110, if too many original components 112 have been replace or removed, etc.

The process 300 shown in FIG. 3 begins at block 302. The process 300 may begin in response to an event, such as when a software application begins execution, or some other operation is to be performed. When the process 300 is initiated, a set of executable program instructions stored on one or more non-transitory computer-readable media (e.g., hard drive, flash memory, removable media, etc.) may be loaded into memory (e.g., random access memory or "RAM") of the device 110. The executable instructions may then be executed by a hardware-based computer processor (e.g., a central processing unit or "CPU") of the computing device. In some embodiments, the process 300 or portions thereof may be implemented on multiple processors, serially or in parallel.

At block 304, the signature manager 130 or some other module or component of the device 110 can obtain identifiers for the components 112 that are present in the device 110. In some embodiments, the signature manager 130 can obtain identifiers 114 for all components 112 of the device 110, or for only certain components 112 (e.g., the n most important components, or the components specified for the function being authorized).

At block 306, the signature manager 130 or some other module or component of the device 110 can obtain secret shares for the identifiers obtained at block 304. In some embodiments the signature manager 130 can query the data store 120 for share data 124 representing the secret shares that correspond to the obtained identifiers 114. There may be more secret shares in the data store 120 than there are identifiers (e.g., if a component 112 was removed but not replaced), there may be more identifiers than secret shares in the data store 120 (e.g., if a component 112 was added without another component being removed), or there may be the same number of secret shares as components (e.g., no components have been added or removed at all or none without the same number of components being removed or added, respectively).

At block 308, the signature manager 130 or some other module or component of the device 110 can generate digital signature shares, also referred to simply as "signature shares," using the secret shares retrieved above at block 306. In some embodiments, the signature manager 130 may generate a separate signature share using each secret share and the same data item. For example, a predefined encryption function may use a secret share to encrypt a data item, such as a message or some other token. The token may be a randomly-generated value, a token provided to the authorization process, or some other input that is to serve as the unencrypted message to be digitally signed. The token may be encrypted directly, or it may be processed first (e.g., a hash may be generated using a hashing algorithm). The output of the encryption function may be an encrypted version of the input value (or hashed input value). Illustratively, the signature manager 130 may use a first secret share to encrypt a token and generate a first signature share. The signature manager 130 may also use a second secret share to encrypt the same token and generate a second signature share. This process may be repeated for each available secret share to generate a set of signature shares from which a digital signature will be generated as described below.

At block 310, the signature manager 130 or some other module or component of the device 110 can obtain verification key data 126 representing the verification key to be used in verifying a digital signature generated using the signature shares generated using the secret shares.

At block 312, the signature manager 130 or some other module or component of the device 110 can generate a digital signature using the signature shares generated above at block 308. In some embodiments, signature shares may be combined to generate the digital signature. For example, signature shares may be multiplied or added together to obtain a digital signature, depending upon the digital signature thresholding scheme being used. Generally described, the signature shares may serve as input into a function that generates a digital signature using the signature shares. The output of the function may be an encrypted version of the token from which the signature shares were generated.

At block 314, the signature manager 130 or some other module or component of the device 110 can verify the digital signature using the verification key. In some embodiments, the signature manager 130 can decrypt the message, generated above at block 312, using a predefined decryption function and the verification key as the decryption key. If the decrypted message matches the original data item (or hash of the original data item), then the correct digital signature was determined. Otherwise, if the decrypted message does not match the original data item (or hash thereof), then an incorrect digital signature was determined.

At decision block 316, the signature manager 130 or some other module or component of the device 110 can determine whether the digital signature was verified above at block 314. If so, the process can proceed to block 318, where the function is authorized. For example, the software that is to be executed may be permitted to execute. If the signature manager 130 determines that the digital signature was not verified above at block 314, then the process may proceed to block 320, where the function is not authorized. For example, the software that is to be executed may not be permitted to execute.

At block 322 the process 300 can terminate.

Threshold-Based Authorization Using Weighted Secret Shares

Figure 4:
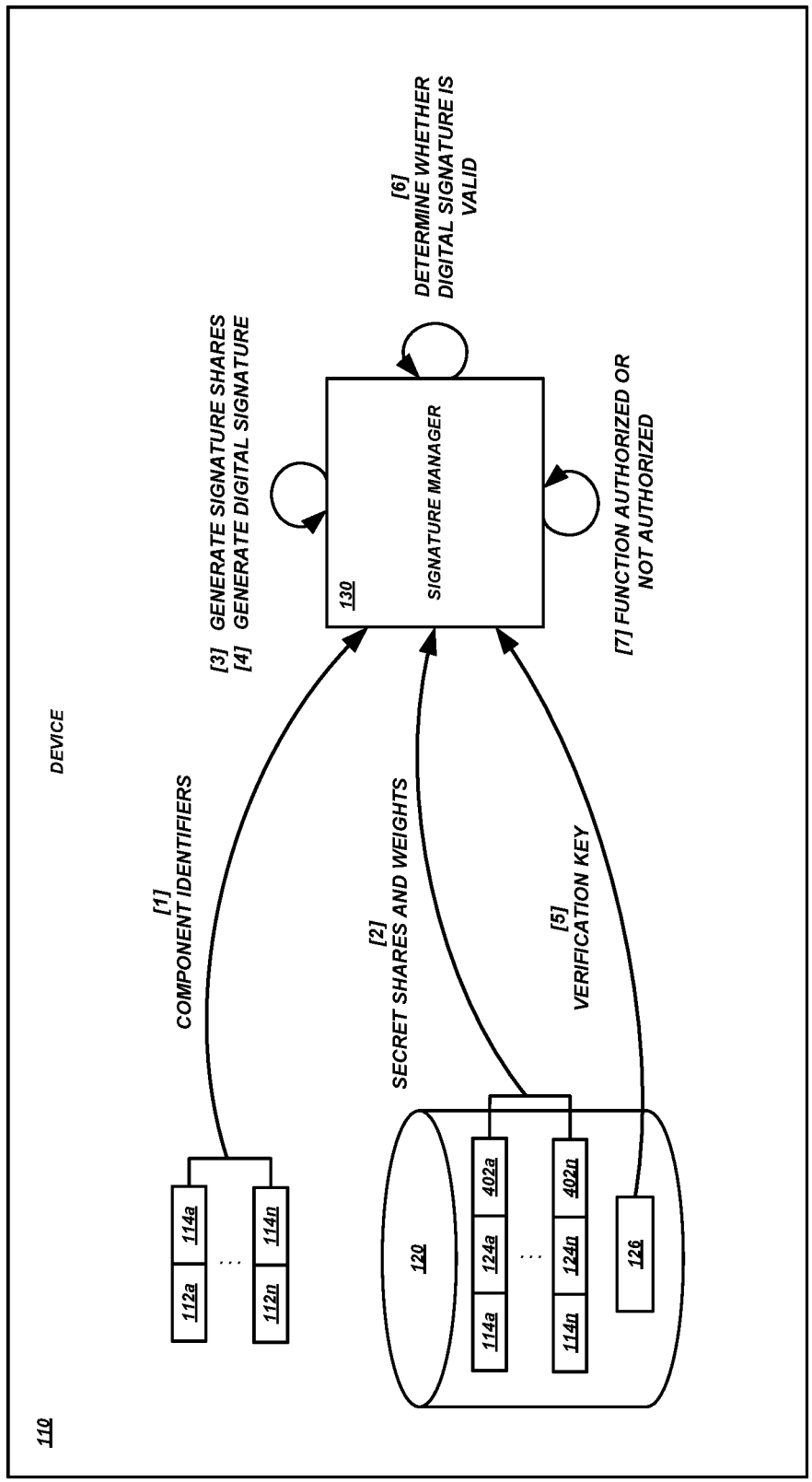
FIG. 4 is a block diagram illustrating data flows and processing performed by a device during weighted authorization according to some embodiments.

FIG. 4 is a block diagram of illustrative data flows and operations of a device 110 during threshold-based authorization using weighted secret shares. The displayed interactions may occur during authorization of a function, or authorization of operation of the device 110 itself. For example, a device 110 may be manufactured with an initial set of components 112. Some components 112 may be more important to the operation of the device 110, such that the device 110 is not permitted to operate without the items, or without particular versions of the items (e.g., original equipment manufacturer or "OEM" versions). Illustratively, the MCU of an infusion pump may be considered important, such that the pump is not permitted to operate without an OEM version. A battery that provides power to the pump when not connected to a wired power source may be considered less important, such that the pump is permitted to operate with a non-OEM version of the battery. However, if too many other parts are non-OEM in addition to the battery, then the pump may not be permitted to operate, even if "important" components like the MCU are present. To facilitate such treatment based on the characterized importance of the components, the individual components may be assigned weighting factors or given variable numbers of secret shares based on their characterized importance. When an authorization process is performed, the threshold amount of secret shares required may be a threshold amount of weighted secret shares based on the weighting factors or sets of secret shares assigned to each present component.

At [1], the signature manager 130 or some other module or component of the device 110 can obtain identifiers for the components that are present in the device 110. In some embodiments, the signature manager 130 can obtain identifiers 114 for all components 112 of the device 110, or for only certain components 112 (e.g., the n most important components, or the components specified for the function being authorized).

At [2], the signature manager 130 or some other module or component of the device 110 can obtain secret shares and weights associated with the component identifiers obtained at [1]. The weights and secret shares may be obtained from a data store 120, a separate data store in the signature manager 130, or some other module or component of the device 110. In some embodiments, the weights and secret shares may have been set and stored on the device 110 when the device 110 was manufactured. For example, the manufacturer may determine the weights according to a heuristic that prioritizes some components over other components by assigning higher weights (e.g., weights between 0.75 and 1.0) to components deemed more important, and lower weight (e.g., weights between 0.5 and 0.75) to components deemed less important. Share data $124a \ldots 124n$ representing secret shares, and weight data $402a \ldots 402n$ representing weights, may be stored in the data store 120 or some other module or component of the device 110. In some embodiments, rather than using different weights to represent the relative importance of the components, the components may instead be assigned a different number of secret shares depending upon their relative importance (e.g., more important components may be assigned more secret shares than less important components). For example, if a component has a weight of 5, then there may be 5 different secret shares allotted to the component, while another component with a weight of 1 may have only 1 share allotted. The example weighting methods described herein are illustrative only, and are not intended to be limiting. In some embodiments, other methods for using weighted secret shares may be used.

At [3], the signature manager 130 or some other module or component of the device 110 can generate digital signature shares, if possible, using the secret shares and weights. In some embodiments, the signature manager 130 may generate a different signature share using the same token and each of the different secret shares, as described in greater detail above.

At [4], the signature manager 130 or some other module or component of the device 110 can generate a digital signature using the signature shares determined above. In some embodiments, a predefined function may use the signature shares to generate the digital signature. The output of the function may be an encrypted version of the input value (or hashed input value) from which the signature shares were generated.

At [5], the signature manager 130 or some other module or component of the device 110 can obtain the verification key data 126 representing the verification key to be used in verifying the digital signature that was generated using the signature shares.

At [6], the signature manager 130 or some other module or component of the device 110 can verify the message using the verification key obtained above. In some embodiments, the signature manager 130 can decrypt the message using a predefined decryption function and the verification key as the decryption key. If the decrypted message matches the original data item (or hash of the original data item), then the correct digital signature was determined. Otherwise, if the decrypted message does not match the original data item (or hash thereof), then an incorrect digital signature was determined.

At [7], the signature manager 130 or some other module or component of the device 110 can determine whether the digital signature was verified above at block 314. If so, the function (or operation of the device 110 itself) is authorized. For example, the device 110 may be permitted to enter a ready state in which the device 110 may be used normally. If the signature manager 130 determines that the digital signature was not verified, then the function (or operation of the device 110 itself) is not authorized. For example, the device 110 may enter a blocked state in which normal operation is blocked.

Threshold-Based Multi-Component Authorization

Figure 5:
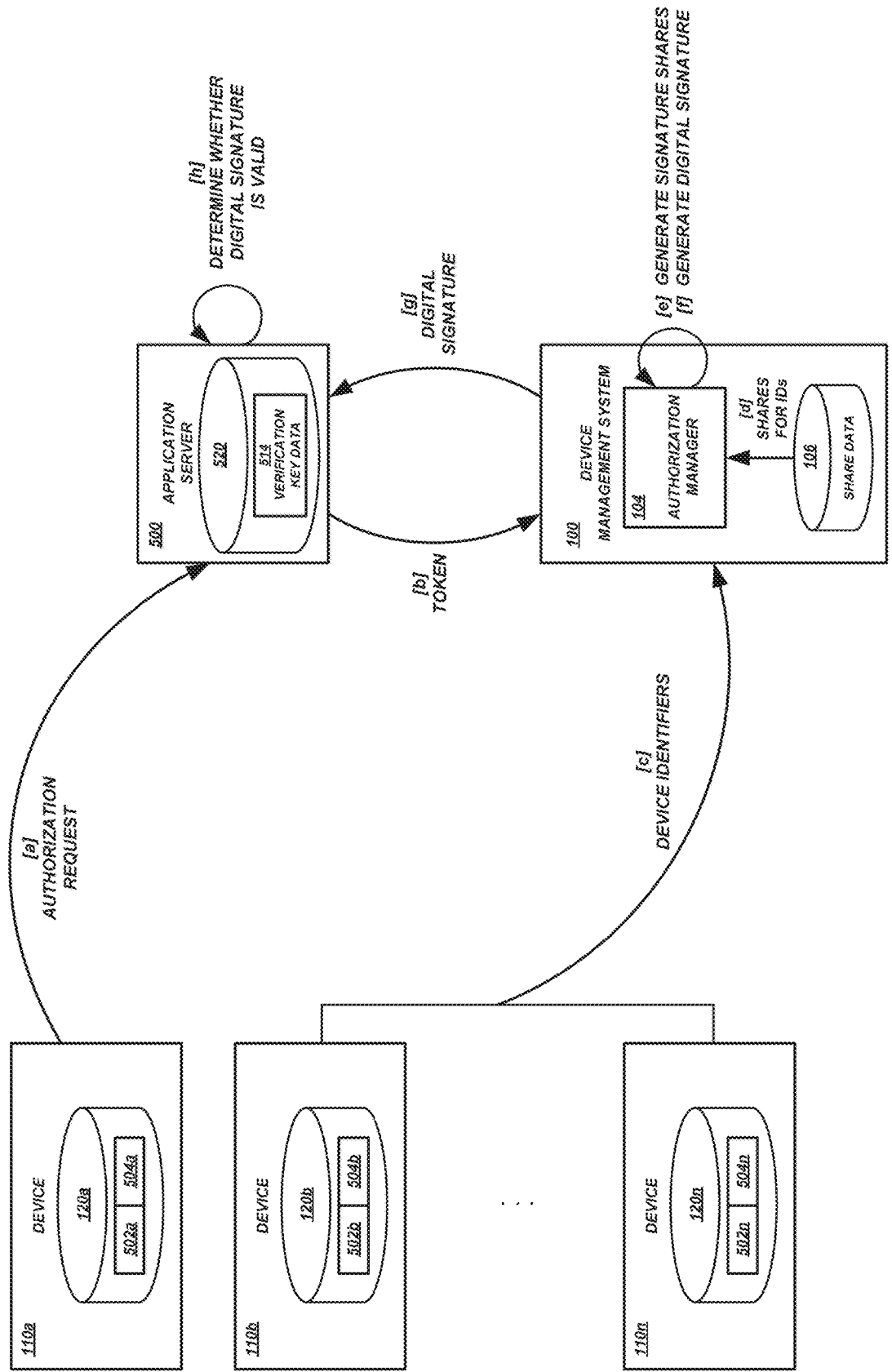
FIG. 5 is a block diagram illustrating data flows and processing performed during group-based authorization according to some embodiments.

FIG. 5 is a block diagram of illustrative data flows and interactions between various devices 110a, 110b, . . . 110n (with data stores 120a, 120b, . . . 120n respectively), a device management system 100, and an application server 500 during threshold-based multi-component authorization (also referred to as "swarm" authentication). The displayed interactions may occur when a device, such as device 110a (which may be associated with identifier 502a and secret share 504a), connects to an application server 500 or otherwise attempts to perform a network operation. The application server 500 (or some other component of the network environment) may block the device 110a from connecting to the application server 500 or performing some other network function until the device 110a is authorized. The authorization process may require a threshold number of other devices 110b, . . . 110n to participate, actively or passively. By requiring the device 110a to be authorized using multiple other devices, the device 110a can be prevented from operating unless it is connected to a network with a threshold number of other devices. This prevents the use of a single device or small number of devices (e.g., devices that may be lost or stolen, or are otherwise being used outside of a multi-device network environment such as a hospital).

At [a], a device 110a attempts to connect to the application server 500 or perform some other network operation that requires the device 110a to first be authenticated. In some embodiments, the device 110a may be medical device, such as an infusion pump, and the application server 500 may be a related clinical system, such as an infusion control server. Illustratively, the infusion control server may instruct infusion pumps regarding the medication to be dispensed, the patient to be treated, the dosage to be infused, the security measures to be implemented, etc. Accordingly, the manufacturer of the infusion pumps may be interested in blocking operation of the infusion pumps (e.g., preventing the pumps from receiving medication dispensing information) unless and until the infusion pumps can first verify that they are part of a proper clinical environment, such as an environment with a threshold number of other such pumps.

At [b], the application server 500 may employ the services of the device management system 100 to authenticate the device 110a. The application server 500 may generate a token or other data to be signed by the device management system 100. The application server 500 may store or otherwise have access to a verification key that can be used to verify the signed message that is received from the device management system 100, as discussed in greater detail below. In some embodiments, the application server 500 may perform some or all of the functions described below as being performed by the device management system 100, or the device management system 100 may perform some or all of the function described as being performed by the application server 500. For example, the application server 500 and device management system 100 may be subsystems of a larger integrated system that includes one or more computing devices configured to perform the disclosed operations.

At [c], the device management system 100 can obtain identifiers and/or corresponding secret shares of the devices 110b . . . 110n that will participate in the multi-device authorization. For example, individual devices 110b . . . 110n can each provide their secret shares 504b . . . 504n to the device management system 100 when the devices 110b . . . 110n boot up, connect to the network environment, connect to the application server 500, are themselves authorized, or the like. As another example, the devices 110b . . . 110n can provide their identifiers 502b . . . 502n (e.g., serial numbers, internet protocol or "IP" addresses, media access control or "MAC" addresses, application-specific identifiers, etc.). The device management system 100 can use the identifiers at [d] to access secret shares corresponding to the devices. As a further example, the device management system 100 may retrieve secret shares and/or identifiers from the devices 110b . . . 110n in response to receiving a token and authentication request, from the application server 500.

The secret shares may be assigned to the devices when the devices are manufactured, when the devices are implemented in the network environment, as the devices are authenticated using a multi-device authorization process, etc. In some embodiments, secret shares may be assigned to devices for periods of time, or secret shares may be revoked in response to the occurrence of particular events. For example, a device 110b may be assigned a secret share for a predetermined or dynamically determined period of time (e.g., 1 hour, 1 day, 1 year, 1 network communication session, etc.) after which the device 110b must be reassigned a share or have its secret share renewed (e.g., upon completion of a multi-device authorization process for the device 110b).

At [e], the authorization manager 104 or some other module or component of the device management system 100 can generate signature shares, if possible, using the secret shares, as discussed in greater detail above. In some embodiments, a predefined encryption function may use individual secret shares to encrypt the same data item, generating a set of signature shares. The data item may be the token or other data received from the application server 500. The data item may be encrypted directly, or it may be processed first (e.g., a hash may be generated using a hashing algorithm). This process may be repeated for each available secret share as described above.

At [f], the authorization manager 104 or some other module or component of the device management system 100 can generate a digital signature using the signature shares determined above. A valid digital signature may only be generated if a threshold number of secret shares, corresponding to a threshold number of devices 110a . . . 110n, are available at the time the authorization process is performed. If there are fewer than the threshold number of secret shares, then a valid digital signature may be impossible or computationally infeasible to determine. In this instance, the authorization process may be aborted, and/or an error message or other failure message may be returned to the application server 500.

At [g], the authorization manager 104 or some other module or component of the device manager 100 can send the digital signature (e.g., the encrypted token) to the application server 500.

At [h], the application server 500 can access (e.g., in data store 520) verification key data 514 representing the verification key, and decrypt the message using a predefined decryption function and the verification key as the decryption key. If the decrypted message matches the original token that was sent to the device manager 100 (or data derived therefrom, such as a hash), then the correct digital signature was determined. In this instance, the device 110*a* may be considered authorized because at least a threshold number of other devices participated in the authorization process. Otherwise, if the decrypted message does not match the original data item (or hash thereof), then an incorrect digital signature was determined. In this instance, the application server 500 may block the device 110*a* from performing the function that the device 110*a* is attempting to perform because the device 110*a* has not been authorized. This may occur when fewer than a threshold number of devices participate in the process, such as when the device 110 is being used outside of an intended clinical environment (e.g., the device is lost, stolen, or sold).

Threshold-Based Security Enforcement Using Weighted Secret Shares

Figure 6:
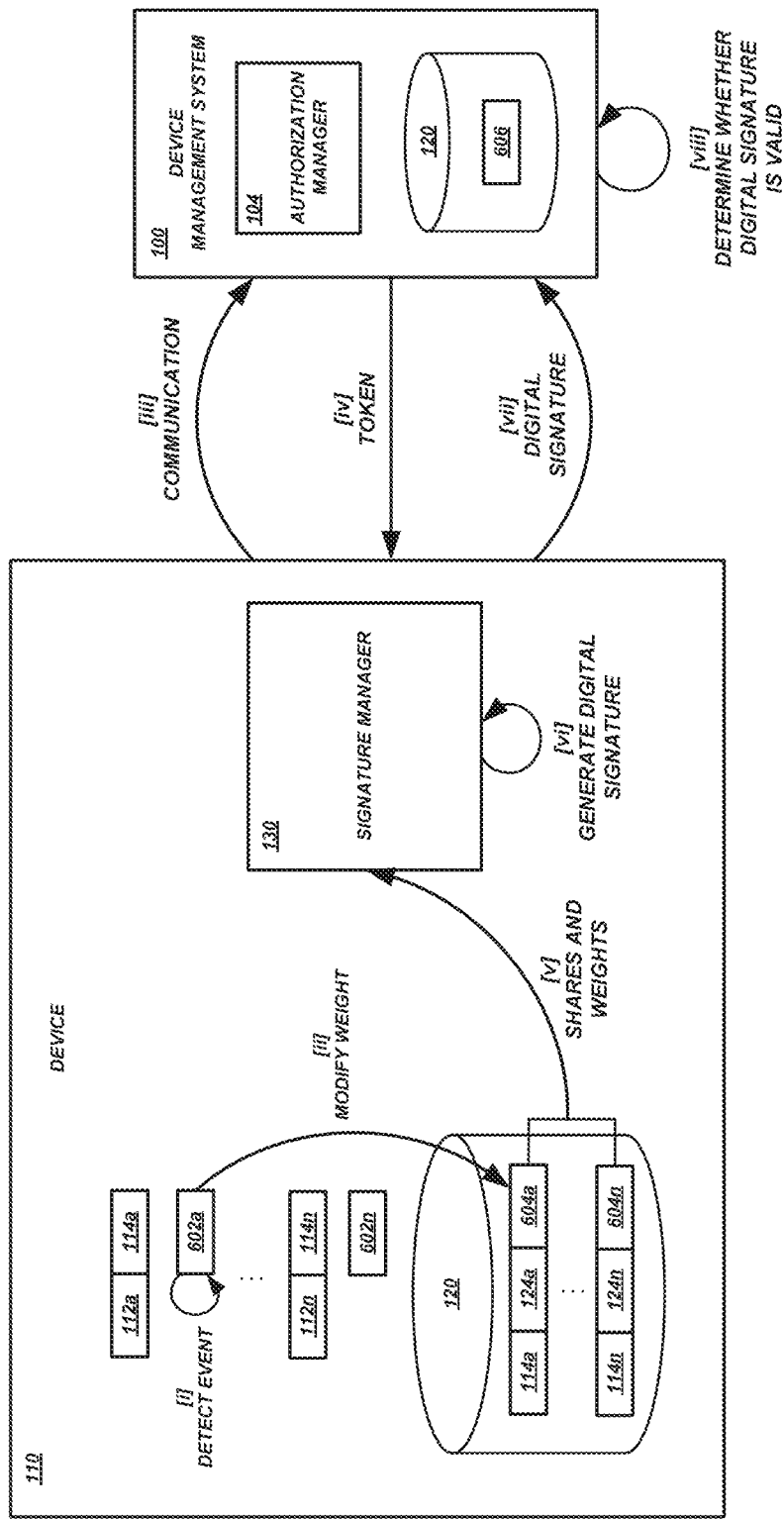
FIG. 6 is a block diagram illustrating data flows and processing performed by a device during dynamic weighted authorization according to some embodiments.

FIG. 6 is a block diagram of illustrative data flows and interactions between a device 110 and a device management system 100 during threshold-based security enforcement. In threshold-based security enforcement, different components of a multi-component system can participate in identifying security risks and enforcing security policies. For example, different components 112 of a single device 110 may participate, different devices 110 of a distributed system may participate, etc. Advantageously, the individual components may each be assigned a weight. As the components (or separate security modules with which the components are associated) detect the occurrence of security events that impact the security of the system, the components can adjust their weighting factors to reflect the impact. For example, if one security monitoring module (also referred to as a security monitor or security module) determines that a security risk has occurred or is likely to occur, the security module may reduce the weighting factor for the component to which the security module is assigned. The secret shares and weighting factors of the various components are used to authorize system functions. The authorization process will fail if enough components have provided lower weights such that a threshold amount of weighted secret shares is not used during the authorization process.

The displayed interactions may occur when a device 110 connects to the device management system 100 or otherwise attempts to perform a network operation. In some embodiments, threshold-based security enforcement may be used when the device 110 communicates with an application server, such as the application server 500 described above.

At [i], a security module (e.g., security module 602*a* or 602*n*) associated with a particular component e.g., component 112*a* or 112*n*, respectively) of the device 110 may determine that a security event has occurred. For example, the security module 602*a* may detect security events such as failed login attempts, medication or dosing alerts, security override events, repeated pings, network scanning activity, denial of service conditions, other alerts or errors, and the like. In some embodiments, the device 110 may be a medical device, such as an infusion pump. In this instance, the component 112*a* may be a component of the infusion pump, such as an MCU, and the security module 602*a* may be assigned to or integrated with the MCU. The security module 602*a* may detect security events such as invalid attempts to infuse medication, alerts indicating an attempt to infuse an unsafe dose, or the like.

At [ii], the security module 602*a* may modify the weight 604*a* based on the security event(s) that the security module 602*a* has detected. The degree to which the weight 604*a* is adjusted may be incremental, or it may be dynamically determined based on the particular event(s) detected. For example, the weight 604*a* may have a starting or default value (e.g., 1.0) when the device 110 begins operation. The security module 602*a* may be configured to lower the weight 604*a* by an incremental amount for each security risk that is detected (e.g., lower the weight by 0.05 for each failed login attempt, each medication dose alarm, etc.). As another example, the security module 602*a* may be configured to lower the weight by a varying amount depending upon the particular security risk identified (e.g., lower the weight by 0.1 after three failed login attempts, lower the weight by 0.2 after two medication dose alarms, etc.).

In some embodiments, the security module 602*a* may increase the weight 604*a* in response to certain events, after the passage of a predetermined or dynamically determined period of time, etc. For example, the security module 602*a* may increase the weight 604*a* after a period of time (e.g., 10 minutes, 1 hour, etc.) has passed without a negative security event occurring. As another example, the security module 602*a* may reset the weight 604*a* to its default value in response to an administrator logging into the system. In some embodiments, the security module 602*a* may only adjust a weight 604*a* between maximum and minimum values (e.g., the weight may not be permitted to fall below 0.0 or rise above 1.0).

The example security events, weighting factor values, and adjustment rules described herein are illustrative only, and are not intended to be limiting. In some embodiments, fewer, additional, and/or alternative events, weighting factor values, and adjustment rules may be used.

At [iii], the device 110 can attempt to perform a particular function, such as connect to the device management system 100 or perform some other network operation that requires the security status of the device 110 to first be validated. For example, if the device 110 is a medical device such as an infusion pump, the device may attempt to infuse medication, connect to a network server to obtain data regarding medications, doses, or patients, etc. Accordingly, the manufacturer of infusion pumps may be interested in blocking operation of the infusion pumps (e.g., preventing the pumps from receiving medication dispensing information) unless and until the security status of the infusion pumps can first be validated.

At [iv], the device management system 100 may generate a token or other data to be signed by the device 110. The device management system 100 may store or otherwise have access to a verification key that can be used to verify the signed message that is received from the device 110, as discussed in greater detail below.

At [v], the signature manager 130 or some other module or component of the device 110 can obtain identifiers and corresponding secret shares and weights for the components 112*a* . . . 112*n*. For example, the signature manager 130 may determine the identifiers 114*a* . . . 114*n* of the components 112*a* . . . 112*n*. The signature manager 130 may then obtain the corresponding secret shares 124a . . . 124n and weights 604a . . . 604n from the data store 120.

At [vi], the signature manager 130 or some other module or component of the device 110 can generate signature shares using the secret shares 124a . . . 124n and weights 604a . . . 604n, as discussed in greater detail above. A digital signature may then be generated using the signature shares. If the amount of weighted secret shares fails to satisfy the threshold amount, then a valid digital signature may be impossible or computationally infeasible to determine. In this instance, the authorization process may be aborted, and/or an error message or other failure message may be returned.

If a threshold number of signature shares are generated, the signature manager 130 can then generate the digital signature, as described in greater detail above.

At [vii], the device 110 can send the signed message (e.g., the encrypted token) to the device management system 100.

At [viii], the device management system 100 can obtain the verification key data 606 representing the verification key, and decrypt the message using a predefined decryption function and the verification key as the decryption key. If the decrypted message matches the original token that was sent to the device management system 100 (or data derived therefrom, such as a hash), then the correct digital signature was determined. In this instance, the device 110 may be considered to be in a secure state because at least a threshold amount of weighted secret shares, as maintained by the various components of the device 110, were available for the authorization process. Otherwise, if the decrypted message does not match the original data item (or hash thereof), then an incorrect digital signature was determined. In this instance, the device management system 100 may block the device 110 from communicating with the device management system 100, other network systems (e.g., application server 500), performing particular operations, etc.

Other Considerations

It is to be understood that not necessarily all objects or advantages may be achieved in accordance with any particular embodiment described herein. Thus, for example, those skilled in the art will recognize that certain embodiments may be configured to operate in a manner that achieves or optimizes one advantage or group of advantages as taught herein without necessarily achieving other objects or advantages as may be taught or suggested herein.

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

The various illustrative logical blocks, modules, and algorithm elements described in connection with the embodiments disclosed herein can be implemented as electronic hardware, computer software, or combinations of both. To clearly illustrate this interchangeability of hardware and software, various illustrative components, blocks, modules, and elements have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a computer processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A computer processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, e.g., a combination of a DSP and a microprocessor, a plurality of microprocessors, one or more microprocessors in conjunction with a DSP core, or any other such configuration. Although described herein primarily with respect to digital technology, a processor may also include primarily analog components. For example, some or all of the signal processing algorithms described herein may be implemented in analog circuitry or mixed analog and digital circuitry. A computing environment can include any type of computer system, including, but not limited to, a computer system based on a microprocessor, a mainframe computer, a digital signal processor, a portable computing device, a device controller, or a computational engine within an appliance, to name a few.

The elements of a method, process, or algorithm described in connection with the embodiments disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC. The ASIC can reside in a user terminal. In the alternative, the processor and the storage medium can reside as discrete components in a user terminal.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements, and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

Disjunctive language such as the phrase "at least one of X, Y, or Z," unless specifically stated otherwise, is otherwise understood with the context as used in general to present that an item, term, etc., may be either X, Y, or Z, or any combination thereof (e.g., X, Y, and/or Z). Thus, such disjunctive language is not generally intended to, and should not, imply that certain embodiments require at least one of X, at least one of Y, or at least one of Z to each be present.

Unless otherwise explicitly stated, articles such as "a", "an", or "the" should generally be interpreted to include one or more described items. Accordingly, phrases such as "a device configured to" are intended to include one or more recited devices. Such one or more recited devices can also be collectively configured to carry out the stated recitations. For example, "a processor configured to carry out recitations A, B, and C" can include a first processor configured to carry out recitation A working in conjunction with a second processor configured to carry out recitations B and C.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments described herein can be implemented within a form that does not provide all of the features and benefits set forth herein, as some features can be used or practiced separately from others. All such modifications and variations are intended to be included herein within the scope of this disclosure. Further, additional embodiments created by combining any two or more features or techniques of one or more embodiments described herein are also intended to be included herein within the scope of this disclosure.

What is claimed is:

1. An infusion pump comprising:
   a security monitor;
   a motor control unit configured to control infusion of medication, wherein the motor control unit is associated with a first component identifier;
   a battery configured to power the infusion pump, wherein the battery is associated with a second component identifier;
   a computer processor programmed with executable instructions, wherein the computer processor is associated with a third component identifier; and
   a data store storing:
      verification key data representing a verification key;
      share data representing a plurality of secret shares for generating a digital signature, wherein a first secret share of the plurality of secret shares is associated with the first component identifier, wherein a second secret share of the plurality of secret shares is associated with the second component identifier, and wherein a third secret share of the plurality of secret shares is associated with the third component identifier; and
      a plurality of weights, wherein individual weights of the plurality of weights are associated with individual secret shares of the plurality of secret shares;
   wherein the computer processor is programmed by the executable instructions to at least:
      determine that a command has been issued for execution of software that controls a function of the infusion pump;
      determine a plurality of component identifiers, wherein individual component identifiers of the plurality of component identifiers correspond to individual components of the infusion pump present at a time the command is issued;
      load at least a subset of the plurality of secret shares based at least partly on the plurality of component identifiers;
      generate a plurality of signature shares using the subset of the plurality of secret shares, wherein a threshold number of weighted shares is required in order to generate a threshold number of signature shares;
      generate the digital signature using the plurality of signature shares;
      verify the digital signature using the verification key; and
      authorize execution of the software; and
   wherein the security monitor is configured to at least:
      detect occurrence of a security event; and
      reduce a value of a weight based at least partly on the security event,
   wherein the weight is associated with a component of the infusion pump, and
   wherein the security monitor is associated with the component of the infusion pump.

2. The infusion pump of claim 1, wherein the security event comprises one of: a failed login attempt, a medication alert, a security override attempt, a repeated ping, network scanning activity, a denial of service event, or an error.

3. The infusion pump of claim 1, wherein the computer processor is further programmed to execute the software in response to authorizing execution of the software, wherein executing the software causes one of: dispensing medication, or communicating with a network server.

4. The infusion pump of claim 1, wherein the computer processor is further programmed to store the first secret share in a secure storage location associated with a corresponding component of the infusion pump.

5. The infusion pump of claim 1, wherein the computer processor is further programmed to store an obfuscated version of the first secret share.

6. The infusion pump of claim 1, wherein a second component of the infusion pump is configured to:
   detect occurrence of a second security event, wherein the security event is an infusion-related event, and wherein the second security event is different from the security event; and
   modify a value of a second weight associated with the second component based at least partly on the second security event.

7. The infusion pump of claim 1, wherein to modify the value of the weight, the security monitor is further configured to:
   determine, based on the security event, a first modification to be applied to the value of the weight, wherein the security event is associated with the first modification, wherein a second security event is associated with a second modification different from the first modification, wherein the security event is an infusion-related event, and wherein the second security event is different from the security event; and apply the first modification to the value of the weight.

8. The infusion pump of claim 1, wherein to reduce the value of the weight, the security monitor is further configured to apply an incremental modification to the value of the weight to produce a modified weight.

9. The infusion pump of claim 8, wherein the security monitor is further configured to:
detect occurrence of a second security event, wherein the security event is an infusion-related event, and wherein the second security event is different from the security event; and
apply the incremental modification.

10. A computer-implemented method comprising:
under control of an infusion system comprising a security monitor, a motor control unit associated with a first component identifier and configured to control infusion of medication, a battery associated with a second component identifier and configured to power the infusion system, a computer processor associated with a third component identifier, a security monitor, and a data store:
determining that a command has been issued for execution of software that controls a function of the infusion system;
determining a plurality of component identifiers, wherein individual component identifiers of the plurality of component identifiers correspond to individual components of the infusion system present at a time the command is issued;
load at least a subset of a plurality of secret shares from the data store based at least partly on the plurality of component identifiers, wherein the data store stores:
verification key data representing a verification key;
share data representing the plurality of secret shares for generating a digital signature, wherein a first secret share of the plurality of secret shares is associated with the first component identifier, wherein a second secret share of the plurality of secret shares is associated with the second component identifier, and wherein a third secret share of the plurality of secret shares is associated with the third component identifier; and
a plurality of weights, wherein individual weights of the plurality of weights are associated with individual secret shares of the plurality of secret shares;
generating a plurality of signature shares using the subset of the plurality of secret shares, wherein a threshold number of weighted shares is required in order to generate a threshold number of signature shares;
generating the digital signature using the plurality of signature shares;

verifying the digital signature using the verification key;
authorizing execution of the software;
detecting occurrence of a security event; and
reducing a value of a weight based at least partly on the security event,
wherein the weight is associated with a component of the infusion system, and wherein the security monitor is associated with the component of the infusion system.

11. The computer-implemented method of claim 10, wherein the security event comprises one of: a failed login attempt, a medication alert, a security override attempt, a repeated ping, network scanning activity, a denial of service event, or an error.

12. The computer-implemented method of claim 10, further comprising executing the software in response to authorizing execution of the software, wherein executing the software causes one of: dispensing medication, or communicating with a network server.

13. The computer-implemented method of claim 10, further comprising storing the first secret share in a secure storage location associated with a corresponding component of the infusion system.

14. The computer-implemented method of claim 10, further comprising storing an obfuscated version of the first secret share.

15. The computer-implemented method of claim 10, further comprising:
detecting occurrence of a second security event, wherein the security event is an infusion-related event, and wherein the second security event is different from the security event; and
modifying a value of a second weight based at least partly on the second security event.

16. The computer-implemented method of claim 10, wherein reducing the value of the weight comprises:
determining, based on the security event, a first modification to be applied to the value of the weight, wherein the security event is associated with the first modification, wherein a second security event is associated with a second modification different from the first modification, wherein the security event is an infusion-related event, and wherein the second security event is different from the security event; and
applying the first modification to the value of the weight.

17. The computer-implemented method of claim 10, wherein reducing the value of the weight comprises applying an incremental modification to the value of the weight to produce a modified weight.

18. The computer-implemented method of claim 17, further comprising:
detecting occurrence of a second security event, wherein the security event is an infusion-related event, and wherein the second security event is different from the security event; and
applying the incremental modification.

\* \* \* \* \*

UNITED STATES PATENT AND TRADEMARK OFFICE
CERTIFICATE OF CORRECTION

PATENT NO. : 12,130,910 B2
APPLICATION NO. : 16/869404
DATED : October 29, 2024
INVENTOR(S) : S. Sree Vivek Page 1 of 1

It is certified that error appears in the above-identified patent and that said Letters Patent is hereby corrected as shown below:

In the Specification

Column 6, Line 30, delete "secret, shares" and insert -- , secret shares --.

Column 6, Line 51, delete "At [13]," and insert -- At [B], --.

Column 6, Line 54, delete "hatch to" and insert -- batch to --.

Column 12, Line 30 (approx.), delete "authentication request," and insert -- authentication request --.

Column 13, Line 61, delete "component e.g.," and insert -- component (e.g., --.

Signed and Sealed this
Fourth Day of February, 2025

Coke Morgan Stewart
*Acting Director of the United States Patent and Trademark Office*